United States Patent
Nesbitt

(10) Patent No.: US 8,940,357 B2
(45) Date of Patent: Jan. 27, 2015

(54) MARKED PRECOATED MEDICAL DEVICE AND METHOD OF MANUFACTURING SAME

(75) Inventor: Bruce Nesbitt, Chicago, IL (US)

(73) Assignee: Innovatech LLC, Chicago, IL (US)

( * ) Notice: Subject to any disclaimer, the term of this patent is extended or adjusted under 35 U.S.C. 154(b) by 36 days.

(21) Appl. No.: 13/535,009

(22) Filed: Jun. 27, 2012

(65) Prior Publication Data

US 2012/0263863 A1 Oct. 18, 2012

Related U.S. Application Data

(63) Continuation of application No. 12/171,847, filed on Jul. 11, 2008, now Pat. No. 8,231,926, which is a continuation-in-part of application No. 11/962,326, filed on Dec. 21, 2007, now Pat. No. 8,048,471.

(51) Int. Cl.
*A61L 33/00* (2006.01)
*A61L 31/10* (2006.01)
(Continued)

(52) U.S. Cl.
CPC ............... *A61L 31/10* (2013.01); *A61L 29/085* (2013.01); *A61L 29/18* (2013.01); *A61L 31/18* (2013.01); *B05D 3/0254* (2013.01); *B05D 5/00* (2013.01);
(Continued)

(58) Field of Classification Search
USPC ........... 523/334; 623/23.71; 602/8; 427/2.31, 427/340; 424/423; 428/413
See application file for complete search history.

(56) References Cited

U.S. PATENT DOCUMENTS

| 1,617,102 A | 2/1927 | Cohn |
| 1,772,846 A | 8/1930 | Spolidoro |

(Continued)

FOREIGN PATENT DOCUMENTS

| EP | 0 321 091 | 6/1989 |
| EP | 0 624 380 | 11/1994 |

(Continued)

OTHER PUBLICATIONS

Acetal (POM) Engineering Property Data, Article, published by Material Property Data, [online] [retrieved from the Internet Nov. 26, 2007] <URL:www.matweb.com/reference/acetalpolymer.aspx>.

(Continued)

*Primary Examiner* — Dah-Wei D Yuan
*Assistant Examiner* — Andrew Bowman
(74) *Attorney, Agent, or Firm* — Neal, Gerber & Eisenberg LLP

(57) ABSTRACT

A medical device, such as a medical wire, which includes a coating applied to the surface of the medical wire. The coating includes a base layer bonded to the surface of the medical wire and an at least partially transparent low-friction top coat applied to the base layer. The base layer includes heat activated pigments that change color when heated above a color shifting temperature. In one embodiment, the color of the pigment in one area contrasts with the color of the pigment in an adjacent area without otherwise affecting the low-friction surface of the coating. The areas of different color created in locations along the length of the low-friction coated medical wire form markings which, as an example, enable a surgeon to determine the length of the medical wire inserted into a body by observing the markings on the portion of the marked medical wire located exterior to the body.

15 Claims, 10 Drawing Sheets

(51) Int. Cl.
  *A61L 29/08* (2006.01)
  *A61L 29/18* (2006.01)
  *A61L 31/18* (2006.01)
  *B05D 3/02* (2006.01)
  *B05D 5/00* (2006.01)
  *B05D 5/08* (2006.01)
  *B05D 7/00* (2006.01)

(52) U.S. Cl.
  CPC . *B05D 5/08* (2013.01); *B05D 7/546* (2013.01); *A61L 2420/02* (2013.01)
  USPC .............. 427/2.1; 523/334; 623/23.71; 602/8; 427/2.31; 427/340; 424/423; 428/413

(56) References Cited

U.S. PATENT DOCUMENTS

| | | |
|---|---|---|
| 2,049,769 A | 8/1936 | Gray |
| 2,241,282 A | 5/1941 | Wackerle |
| 2,241,283 A | 5/1941 | Wackerle |
| 2,735,258 A | 2/1956 | Crandall |
| 2,861,417 A | 11/1958 | Crandall |
| 2,892,374 A | 6/1959 | Ralls, Jr. |
| 3,085,912 A | 4/1963 | Friese |
| 3,099,595 A | 7/1963 | Allbaugh |
| 3,120,144 A | 2/1964 | Bayer |
| 3,706,883 A | 12/1972 | McIntyre |
| 3,812,842 A | 5/1974 | Rodriguez |
| 3,857,934 A | 12/1974 | Bernstein et al. |
| 4,003,369 A | 1/1977 | Heilman et al. |
| 4,008,351 A | 2/1977 | Inoue et al. |
| 4,016,714 A | 4/1977 | Crandall, Jr. |
| 4,080,706 A | 3/1978 | Heilman et al. |
| 4,336,087 A | 6/1982 | Martuch et al. |
| 4,377,620 A | 3/1983 | Alexander |
| 4,382,358 A | 5/1983 | Tappe et al. |
| 4,539,228 A | 9/1985 | Lazarus |
| 4,540,628 A | 9/1985 | Oberdeck et al. |
| 4,570,170 A | 2/1986 | Hiraishi et al. |
| 4,577,637 A | 3/1986 | Mueller, Jr. |
| 4,645,491 A | 2/1987 | Evans |
| 4,724,846 A | 2/1988 | Evans, III |
| 4,779,628 A | 10/1988 | Machek |
| 4,796,637 A | 1/1989 | Mascuch et al. |
| 4,799,496 A | 1/1989 | Hargreaves et al. |
| 4,846,193 A | 7/1989 | Tremulis et al. |
| 4,854,330 A | 8/1989 | Evans, III et al. |
| 4,875,489 A | 10/1989 | Messner et al. |
| 4,895,168 A | 1/1990 | Machek |
| 4,922,923 A | 5/1990 | Gambale et al. |
| 4,951,686 A | 8/1990 | Herlitze |
| 4,966,163 A | 10/1990 | Kraus et al. |
| 5,034,005 A | 7/1991 | Appling |
| 5,038,458 A | 8/1991 | Wagoner et al. |
| 5,063,935 A | 11/1991 | Gambale |
| 5,084,022 A | 1/1992 | Claude |
| 5,091,284 A | 2/1992 | Bradfield |
| 5,107,852 A | 4/1992 | Davidson et al. |
| 5,114,401 A | 5/1992 | Stuart et al. |
| 5,117,838 A | 6/1992 | Palmer et al. |
| 5,117,839 A | 6/1992 | Dance |
| 5,144,959 A | 9/1992 | Gambale et al. |
| 5,149,965 A | 9/1992 | Marks |
| 5,154,705 A | 10/1992 | Fleischhacker et al. |
| 5,165,013 A | 11/1992 | Faris |
| 5,165,421 A | 11/1992 | Fleischhacker et al. |
| 5,174,302 A | 12/1992 | Palmer |
| 5,203,777 A | 4/1993 | Lee |
| 5,211,636 A | 5/1993 | Mische |
| 5,234,002 A | 8/1993 | Chan |
| 5,241,970 A | 9/1993 | Johlin, Jr. et al. |
| 5,243,996 A | 9/1993 | Hall |
| 5,260,985 A | 11/1993 | Mosby |
| 5,265,622 A | 11/1993 | Barbere |
| 5,267,955 A | 12/1993 | Hanson |
| 5,271,415 A | 12/1993 | Foerster et al. |
| 5,273,526 A | 12/1993 | Dance et al. |
| 5,279,546 A | 1/1994 | Mische et al. |
| 5,279,573 A | 1/1994 | Klosterman |
| 5,282,478 A | 2/1994 | Fleischhaker, Jr. et al. |
| 5,300,048 A | 4/1994 | Drewes, Jr. et al. |
| 5,345,945 A | 9/1994 | Hodgson et al. |
| 5,353,808 A | 10/1994 | Viera |
| 5,360,403 A | 11/1994 | Mische |
| 5,373,619 A | 12/1994 | Fleischhacker et al. |
| 5,376,083 A | 12/1994 | Mische |
| 5,379,779 A | 1/1995 | Rowland et al. |
| 5,409,004 A | 4/1995 | Sloan |
| 5,433,200 A | 7/1995 | Fleischhacker, Jr. |
| 5,443,081 A | 8/1995 | Klosterman |
| D363,544 S | 10/1995 | Rowland et al. |
| D363,776 S | 10/1995 | Rowland et al. |
| 5,479,938 A | 1/1996 | Weier |
| 5,497,783 A | 3/1996 | Urick et al. |
| 5,497,786 A | 3/1996 | Urick |
| 5,498,250 A | 3/1996 | Prather |
| 5,546,958 A | 8/1996 | Thorud et al. |
| 5,551,444 A | 9/1996 | Finlayson |
| 5,559,297 A | 9/1996 | Yoshikawa et al. |
| 5,606,981 A | 3/1997 | Tartacower et al. |
| 5,610,348 A | 3/1997 | Aladin et al. |
| 5,634,897 A | 6/1997 | Dance et al. |
| 5,640,970 A | 6/1997 | Arenas |
| 5,665,103 A | 9/1997 | Lafontaine et al. |
| 5,669,878 A | 9/1997 | Dickinson et al. |
| 5,713,351 A | 2/1998 | Billings et al. |
| 5,724,989 A | 3/1998 | Dobson |
| 5,728,042 A | 3/1998 | Schwager |
| H1715 H | 4/1998 | Longeat |
| 5,740,473 A | 4/1998 | Tanaka et al. |
| 5,741,267 A | 4/1998 | Jorneus et al. |
| 5,759,174 A | 6/1998 | Fischell et al. |
| 5,782,811 A | 7/1998 | Samson et al. |
| 5,801,319 A | 9/1998 | Hebestreit |
| 5,804,633 A | 9/1998 | Loftin et al. |
| 5,807,279 A | 9/1998 | Viera |
| 5,830,155 A | 11/1998 | Frechette et al. |
| 5,836,892 A | 11/1998 | Lorenzo |
| 5,876,783 A | 3/1999 | Dobson |
| 5,883,319 A | 3/1999 | Hebestreit |
| 5,885,227 A | 3/1999 | Finlayson |
| 5,897,819 A | 4/1999 | Miyata et al. |
| 5,898,117 A | 4/1999 | Ishida |
| 5,907,113 A | 5/1999 | Hebestreit |
| 5,908,413 A | 6/1999 | Lange et al. |
| 5,919,126 A | 7/1999 | Armini |
| 5,919,170 A | 7/1999 | Woessner |
| 5,941,706 A | 8/1999 | Ura |
| 5,948,489 A | 9/1999 | Hopkins |
| 5,970,119 A | 10/1999 | Hofmann |
| 5,984,877 A | 11/1999 | Fleischhacker, Jr. |
| 6,036,682 A | 3/2000 | Lange et al. |
| 6,042,605 A | 3/2000 | Martin et al. |
| 6,048,620 A | 4/2000 | Zhong |
| 6,050,958 A | 4/2000 | Dickinson et al. |
| 6,083,167 A | 7/2000 | Fox et al. |
| 6,093,157 A | 7/2000 | Chandrasekaran |
| 6,093,678 A | 7/2000 | Hamada et al. |
| 6,113,576 A | 9/2000 | Dance et al. |
| 6,139,540 A | 10/2000 | Rost et al. |
| 6,140,267 A | 10/2000 | Gundjian |
| 6,143,013 A | 11/2000 | Samson et al. |
| 6,168,570 B1 | 1/2001 | Ferrera |
| 6,179,788 B1 | 1/2001 | Sullivan |
| 6,193,706 B1 | 2/2001 | Thorud et al. |
| 6,211,450 B1 | 4/2001 | Ishida |
| 6,238,847 B1 | 5/2001 | Axtell, III et al. |
| 6,248,942 B1 | 6/2001 | Hebestreit et al. |
| 6,273,858 B1 | 8/2001 | Fox et al. |
| 6,277,108 B1 | 8/2001 | Mcbroom et al. |
| 6,306,105 B1 | 10/2001 | Rooney et al. |
| 6,315,790 B1 | 11/2001 | Gerberding et al. |
| 6,340,368 B1 | 1/2002 | Verbeck |
| 6,348,646 B1 | 2/2002 | Parker et al. |

(56) References Cited

U.S. PATENT DOCUMENTS

| | | |
|---|---|---|
| 6,355,058 B1 | 3/2002 | Pacetti et al. |
| 6,361,557 B1 | 3/2002 | Gittings et al. |
| 6,370,304 B1 | 4/2002 | Mills et al. |
| 6,387,060 B1 | 5/2002 | Jalisi |
| 6,402,777 B1 | 6/2002 | Globerman et al. |
| 6,425,927 B1 | 7/2002 | Haupt-Stephan et al. |
| 6,428,512 B1 | 8/2002 | Anderson et al. |
| 6,468,079 B1 | 10/2002 | Fischer et al. |
| 6,475,169 B2 | 11/2002 | Ferrera |
| 6,491,646 B1 | 12/2002 | Blackledge |
| 6,501,827 B1 | 12/2002 | Takasawa |
| 6,501,992 B1 | 12/2002 | Belden et al. |
| 6,503,310 B1 | 1/2003 | Sullivan |
| 6,520,923 B1 | 2/2003 | Jalisi |
| 6,520,934 B1 | 2/2003 | Lee et al. |
| 6,528,709 B2 | 3/2003 | Hebestreit et al. |
| 6,540,721 B1 | 4/2003 | Voyles et al. |
| 6,554,942 B2 | 4/2003 | Solar et al. |
| 6,605,049 B1 | 8/2003 | Wagner et al. |
| 6,612,998 B2 | 9/2003 | Gosiengfiao et al. |
| 6,613,002 B1 | 9/2003 | Clark et al. |
| 6,617,515 B1 | 9/2003 | Yeung |
| 6,619,778 B2 | 9/2003 | Igarashi |
| 6,620,114 B2 | 9/2003 | Vrba et al. |
| 6,623,504 B2 | 9/2003 | Vrba et al. |
| 6,626,869 B1 | 9/2003 | Bint |
| 6,635,082 B1 | 10/2003 | Hossainy et al. |
| 6,636,758 B2 | 10/2003 | Sanchez et al. |
| 6,638,589 B1 | 10/2003 | Jarvenkyla |
| 6,652,568 B1 | 11/2003 | Becker et al. |
| 6,652,579 B1 | 11/2003 | Cox et al. |
| 6,673,025 B1 | 1/2004 | Richardson et al. |
| 6,679,853 B1 | 1/2004 | Jalisi |
| 6,680,121 B2 | 1/2004 | Sakoske et al. |
| 6,733,503 B2 | 5/2004 | Layrolle et al. |
| 6,758,857 B2 | 7/2004 | Cioanta et al. |
| 6,765,136 B2 | 7/2004 | Van Pamel |
| D496,728 S | 9/2004 | Holsinger |
| 6,811,805 B2 | 11/2004 | Gilliard et al. |
| 6,811,958 B2 | 11/2004 | Iwami et al. |
| 6,835,454 B1 | 12/2004 | Randa et al. |
| 6,855,161 B2 | 2/2005 | Boylan et al. |
| 6,942,652 B1 | 9/2005 | Pressly, Sr. et al. |
| 6,994,883 B2 | 2/2006 | Layrolle et al. |
| 7,022,086 B2 | 4/2006 | Her |
| 7,033,325 B1 | 4/2006 | Sullivan |
| 7,147,634 B2 | 12/2006 | Nesbitt |
| 7,150,756 B2 | 12/2006 | Levinson et al. |
| 7,153,277 B2 | 12/2006 | Skujins et al. |
| 7,160,297 B2 | 1/2007 | Nesbitt |
| 7,163,509 B2 | 1/2007 | Abe |
| 7,182,757 B2 | 2/2007 | Miyata et al. |
| 7,217,876 B2 | 5/2007 | Allen et al. |
| 7,241,406 B2 | 7/2007 | Solar et al. |
| 7,255,685 B2 | 8/2007 | Pressly, Sr. et al. |
| 7,261,925 B2 | 8/2007 | Nesbitt |
| 7,278,973 B2 | 10/2007 | Iwami |
| 7,288,091 B2 | 10/2007 | Nesbitt |
| 7,296,333 B2 | 11/2007 | Jalisi |
| 7,309,235 B2 | 12/2007 | Wilk |
| 7,311,714 B1 | 12/2007 | Wascher |
| 7,390,326 B2 | 6/2008 | Nesbitt |
| 7,399,296 B2 | 7/2008 | Poole et al. |
| 7,408,101 B2 | 8/2008 | Shelton |
| 7,410,665 B2 | 8/2008 | Ragheb et al. |
| 7,434,437 B2 | 10/2008 | Kato et al. |
| 7,455,646 B2 | 11/2008 | Richardson et al. |
| 7,458,941 B2 | 12/2008 | Caillouette |
| 7,473,417 B2 | 1/2009 | Zeltinger et al. |
| 7,517,342 B2 | 4/2009 | Scott et al. |
| 7,714,217 B2 | 5/2010 | Nesbitt |
| 8,187,206 B2 | 5/2012 | Kinoshita et al. |
| 8,206,320 B2 | 6/2012 | Deal et al. |
| 8,292,872 B2 | 10/2012 | Soetermans |
| 2002/0082681 A1 | 6/2002 | Boylan et al. |
| 2002/0087098 A1 | 7/2002 | Iwami et al. |
| 2002/0136893 A1 | 9/2002 | Schlesinger |
| 2003/0032896 A1 | 2/2003 | Bosley, Jr. et al. |
| 2003/0060731 A1 | 3/2003 | Fleischhacker |
| 2003/0060783 A1 | 3/2003 | Koole et al. |
| 2003/0060872 A1 | 3/2003 | Gomringer et al. |
| 2003/0109865 A1 | 6/2003 | Greep et al. |
| 2003/0120302 A1 | 6/2003 | Minck, Jr. et al. |
| 2003/0139764 A1 | 7/2003 | Levinson et al. |
| 2003/0190478 A1* | 10/2003 | Kutsuna et al. ............... 428/413 |
| 2003/0199759 A1 | 10/2003 | Richard |
| 2003/0203991 A1* | 10/2003 | Schottman et al. ........... 523/334 |
| 2003/0216642 A1 | 11/2003 | Pepin et al. |
| 2003/0229298 A1 | 12/2003 | Iwami et al. |
| 2004/0044399 A1 | 3/2004 | Ventura |
| 2004/0122509 A1 | 6/2004 | Brodeur |
| 2004/0220608 A1 | 11/2004 | D'aquanni et al. |
| 2004/0253185 A1 | 12/2004 | Herweck et al. |
| 2004/0267161 A1 | 12/2004 | Osborne et al. |
| 2005/0003103 A1 | 1/2005 | Krupa |
| 2005/0011332 A1 | 1/2005 | Dronge |
| 2005/0013842 A1* | 1/2005 | Qiu et al. ...................... 424/423 |
| 2005/0038500 A1 | 2/2005 | Boylan et al. |
| 2005/0070821 A1 | 3/2005 | Deal et al. |
| 2005/0080358 A1 | 4/2005 | Iwami et al. |
| 2005/0087520 A1 | 4/2005 | Wang et al. |
| 2005/0133941 A1 | 6/2005 | Schuhmacher |
| 2005/0148902 A1 | 7/2005 | Minar et al. |
| 2005/0154075 A1 | 7/2005 | Siegel |
| 2005/0165472 A1 | 7/2005 | Glocker |
| 2005/0187466 A1 | 8/2005 | Glocker et al. |
| 2005/0261670 A1 | 11/2005 | Weber et al. |
| 2005/0288773 A1 | 12/2005 | Glocker et al. |
| 2006/0036316 A1 | 2/2006 | Zeltinger et al. |
| 2006/0118612 A1 | 6/2006 | Christoffersen et al. |
| 2006/0149165 A1 | 7/2006 | Kennedy et al. |
| 2006/0174745 A1 | 8/2006 | D'Addario |
| 2006/0174746 A1 | 8/2006 | Everly |
| 2006/0184112 A1 | 8/2006 | Horn et al. |
| 2006/0211952 A1 | 9/2006 | Kennedy, II |
| 2006/0257653 A1 | 11/2006 | Tsujimoto et al. |
| 2006/0259033 A1 | 11/2006 | Nesbitt |
| 2006/0271135 A1 | 11/2006 | Minar et al. |
| 2006/0276910 A1* | 12/2006 | Weber ......................... 623/23.71 |
| 2007/0021811 A1 | 1/2007 | D'aquanni et al. |
| 2007/0043333 A1 | 2/2007 | Kampa et al. |
| 2007/0093811 A1 | 4/2007 | Nesbitt |
| 2007/0100279 A1 | 5/2007 | Bates |
| 2007/0118113 A1 | 5/2007 | Nesbitt |
| 2007/0178133 A1* | 8/2007 | Rolland ......................... 424/423 |
| 2007/0207182 A1 | 9/2007 | Weber et al. |
| 2007/0208373 A1 | 9/2007 | Zaver et al. |
| 2007/0212547 A1 | 9/2007 | Fredrickson et al. |
| 2007/0255189 A1* | 11/2007 | Halanski et al. .................. 602/8 |
| 2007/0266542 A1 | 11/2007 | Melsheimer |
| 2008/0008654 A1 | 1/2008 | Clarke et al. |
| 2008/0027532 A1 | 1/2008 | Boylan et al. |
| 2008/0032060 A1 | 2/2008 | Nesbitt |
| 2008/0033373 A1 | 2/2008 | Koole et al. |
| 2008/0050509 A1 | 2/2008 | Nesbitt |
| 2008/0108974 A1 | 5/2008 | Yee |
| 2008/0228109 A1 | 9/2008 | Kinoshita et al. |
| 2008/0288056 A1 | 11/2008 | Simpson et al. |
| 2009/0162530 A1 | 6/2009 | Nesbitt |
| 2009/0163833 A1 | 6/2009 | Kinoshita et al. |
| 2009/0181156 A1 | 7/2009 | Nesbitt et al. |
| 2009/0211909 A1 | 8/2009 | Nesbitt |

FOREIGN PATENT DOCUMENTS

| | | |
|---|---|---|
| EP | 0 771 572 | 5/1997 |
| EP | 0 832 664 | 4/1998 |
| EP | 0 987 042 | 3/2000 |
| EP | 0 749 334 | 6/2000 |
| EP | 1 025 811 | 8/2000 |
| EP | 1 062 965 | 12/2000 |
| EP | 0 833 676 | 9/2003 |
| EP | 1 433 438 | 6/2004 |
| WO | WO/95/14501 | 6/1995 |

(56) References Cited

FOREIGN PATENT DOCUMENTS

| WO | WO/01/45592 | 6/2001 |
|---|---|---|
| WO | WO/02/47549 | 6/2002 |
| WO | WO/2004/033016 | 4/2004 |
| WO | WO 2004/049970 | 6/2004 |
| WO | WO/2004/110519 | 12/2004 |
| WO | WO/2005/094486 | 10/2005 |
| WO | WO/2005/122961 | 12/2005 |
| WO | WO/2006/002199 | 1/2006 |
| WO | WO 2006/006971 | 1/2006 |
| WO | WO 2006/019983 | 2/2006 |
| WO | WO/2007/100556 | 9/2007 |
| WO | WO/2008/097359 | 8/2008 |

OTHER PUBLICATIONS

Advancements in Laser Marking of Plastics, Article, published by The Sabreen Group, Inc., prior to Jul. 2008.
Aug. 5, 2010 Office Action for U.S. Appl. No. 12/766,426.
ClearClad: "Electrophoretic Coating", pp. 1-4, 1996-2002.
Dec. 23, 2009 Office Action for U.S. Appl. No. 12/402,218.
Hydrophilic Coatings, Product Leaflet, published by MCTec, [online] [retrieved from the Internet Nov. 2, 2008] <URL:www.mctecbv.com>.
International Preliminary Report on Patentability, dated Jan. 11, 2011 for PCT/US2009/042697.
International Search Report and the Written Opinion of the International Searching Authority dated Jun. 22, 2009 for PCT/US09/42697.
International Search Report for Application No. PCT/US08/83604 mailed on Jan. 21, 2009.
Marking Processes for Use in Harsh Environments, Article, published by The Sabreen Group, Inc., [online] [retrieved from the Internet Nov. 26, 2007] <URL:www.plasticslasermarking.com/laser_marking_harsh_environments.htm>.
Nagaoka et al., "Low Friction Hydrophillic Surface for medical Device", BioMaterials, Aug. 11, 1990 pp. 419-424.
Office Action of U.S. Appl. No. 11/962,326 dated Oct. 20, 2009.
Office Action of U.S. Appl. No. 12/211,630 dated Aug. 18, 2009.
Plastics Laser Marking in the Aerospace Industry, Article, published by The Sabreen Group, Inc., [online] [retrieved from the Internet Nov. 26, 2007] <URL:www.plasticslasermarking.com/laser_marking_aerospace.htm>.
Sabreen, Scott R., New Technologies for High-Speed Color Laser Marking of Plastics, Article, published by Plastics Decorating Magazine, Oct./Nov. 2004.
Total solutions for High Contrast & Color Laser Marking, Article, Published by The Sabreen Group, Inc., [online] [retrieved from the Internet Nov. 26, 2007] <URL:www.plasticslasermarking.com/metals_laser_marking.htm>.
Total Solutions for High Contrast Laser Marking of Plastics and Metals Substrates, Article, published by The Sabreen Group, Inc., [online] [retrieved from the Internet Nov. 26, 2007] <URL:www.plasticslasermarking.com/laser_marking.htm>.
UV40 Dual Care Acrylated Urethane Coating Technical Data Sheet: Chase Specialty Coatings, pp. 1-3, Jul. 2007.
Office Action for U.S. Appl. No. 13/541,010, dated Mar. 20, 2013.

\* cited by examiner

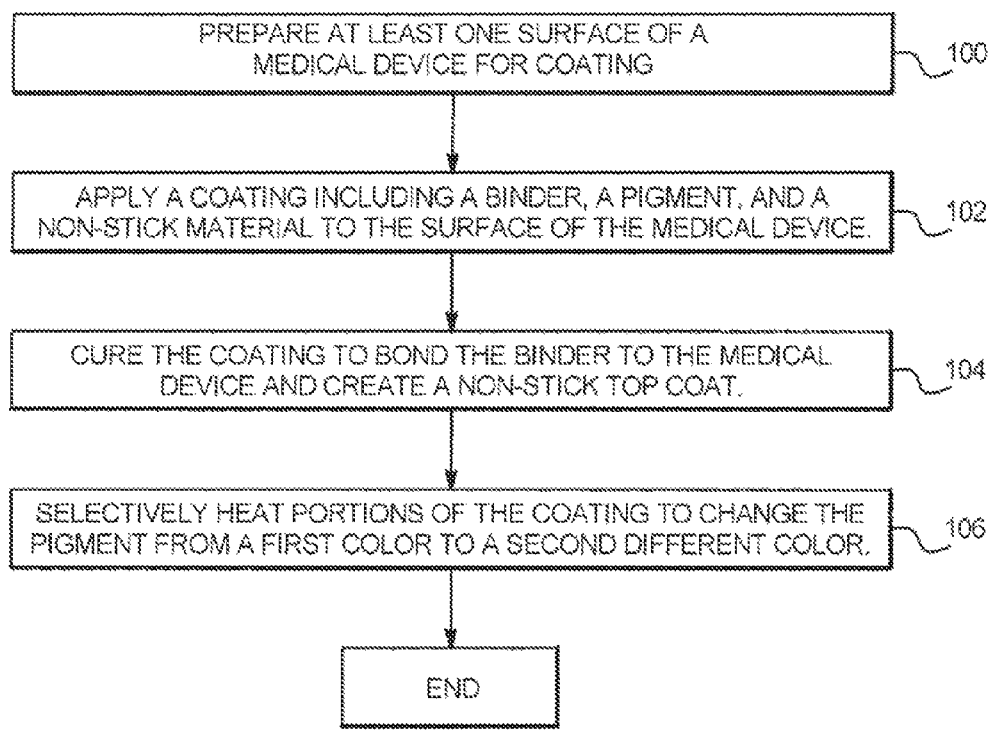

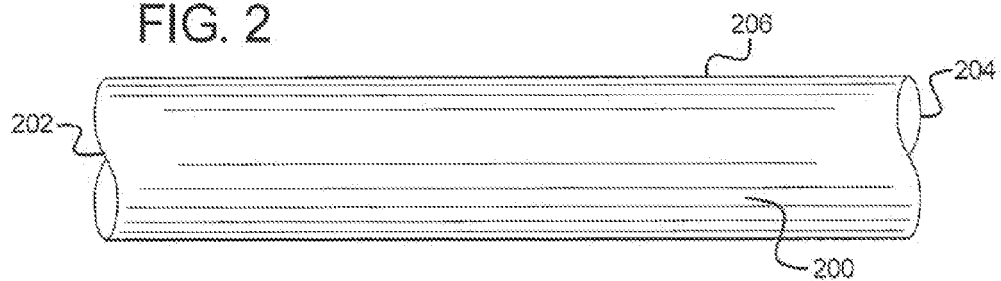
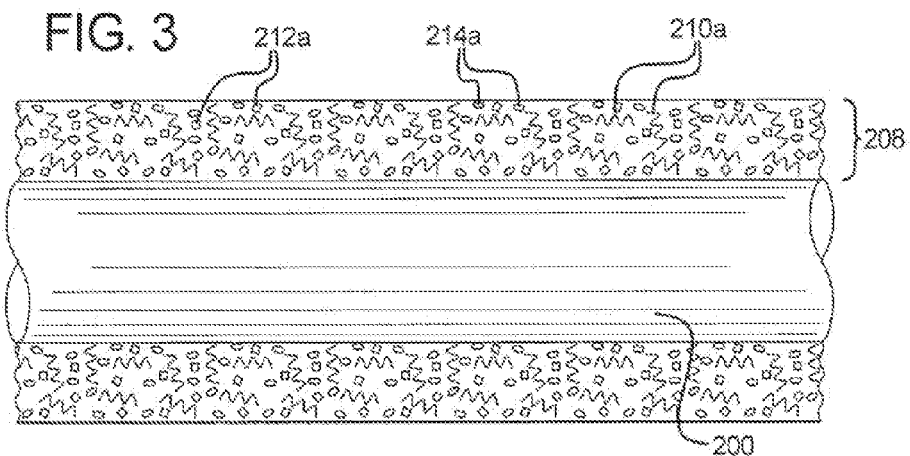
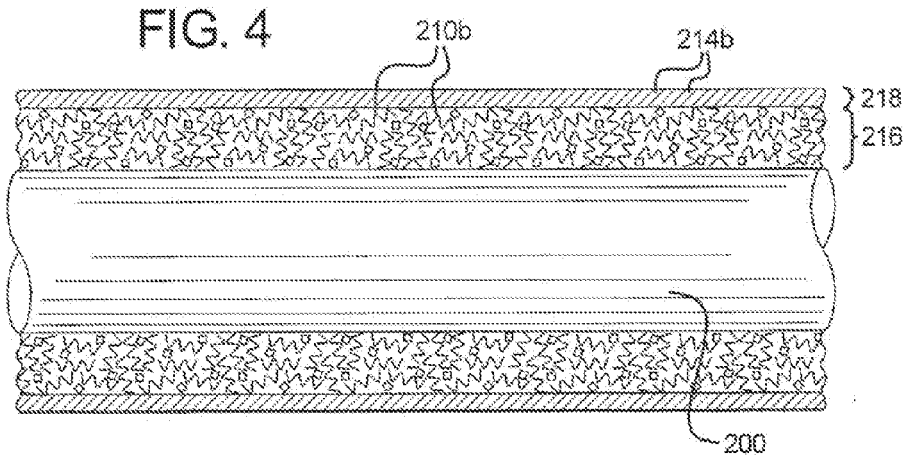

MARKED PRECOATED MEDICAL DEVICE AND METHOD OF MANUFACTURING SAME

PRIORITY CLAIM

This application is a continuation of, claims the benefit of and priority to U.S. patent application Ser. No. 12/171,847, filed on Jul. 11, 2008, which is a continuation-in-part of, claims the benefit of and priority to U.S. patent application Ser. No. 11/962,326, filed on Dec. 21, 2007, the entire contents of each are incorporated by reference herein.

BACKGROUND

Medical devices such as wires, guide wires, probes, mandrels, needles, cannulas, and other medical devices are commonly inserted into humans or animals for therapeutic and diagnostic medical procedures. Often, surgeons or other medical professionals must be able to determine the specific distance that a medical device is inserted into a body. The accurate placement of the medical device is often critical to the procedure. If a medical device is inserted too far into a patient, it could tear, puncture, or otherwise cause damage to internal bodily tissues, vessels, and other organs, which could be harmful or potentially fatal to the patient. Alternatively, if not inserted far enough, the procedure may not be successfully performed. Accordingly, certain medical devices are marked with visual indicia at measured intervals along the length of the device to indicate the length of the medical device inserted into a patient.

Additionally, many medical devices are coated with one or more low friction materials such as polytetrafluoroethylene (PTFE). Low friction, low surface energy coatings reduce the amount of friction between the medical device and bodily tissues, catheters, or other surfaces. Without low friction coatings, certain medical devices are more likely to "stick" to tissues, catheters, or other surfaces during insertion or extraction. If a medical device sticks to other surfaces as it is inserted into a body, a surgeon or other medical professional must apply a greater insertion force to the medical device to reinitiate movement. Once movement is reinitiated, the opposing force immediately decreases so that the medical device is caused to quickly accelerate into the body. Such extreme movements increase the risk of scraping, rubbing, tearing, puncturing, or otherwise damaging a patient's internal tissues due to misplacing the end of the device in the patient. Low friction coatings are less likely to stick to other surfaces and therefore give surgeons or other medical professionals more control or modulate over the insertion speed and depth, which reduces the risk of damage to the patient, thus reducing the "slip-stick" phenomena. Additionally, low friction coatings generally have smooth surfaces that will not scrape, irritate, or snag tissues, vessels or arteries. However, there are very limited methods for marking such devices with low friction coatings.

One known method of marking low friction coated medical devices is to grind, ablate or acid remove the low friction coating to expose the surface of the medical device so that the contrast between the color of the low friction coating and the base metal or surface of the medical device can serve as visual indicia. Ablation is typically achieved by using corrosive chemicals or laser beams, or grinding or grit blasting to selectively remove the coating from the medical device. Such ablation or grinding methods remove the entire coating from the surface of the device, which creates grooves or valleys in the surface of the low-friction or other coating. The shoulders of these grooves or valleys can have sharp edges, particularly when laser beams, grinding, or other similar techniques are used to remove the coating. The resulting sharp edges can scrape bodily tissues, snag vessels or arteries of the patient, or otherwise cause damage and/or trauma to the patient. When inserting medical devices into delicate areas such as the brain and heart, damage caused by the sharp shoulders of the grooves or valleys can be harmful and potentially fatal for the patient. Even if the shoulders are shaped to reduce or eliminate sharp edges, this method of marking low friction coated medical devices still removes the benefits of the low friction coating and exposes the raw, unprotected surface of the medical device, particularly when a wire device changes directions or goes around a turn in a vessel, vein or artery. As described above, the exposed surface of the medical device (and especially any large exposed surfaces of the medical device) is more likely to stick to bodily tissues and other surfaces, potentially harming the patient. Additionally, this method of marking low friction coated medical devices creates different diameters along the length of the medical device which can also increase the required insertion force and decrease the control a surgeon or other medical professional can exercise over the speed and depth of an insertion. Therefore, the above method of marking low friction coated medical devices adversely affects the function of the coated medical device and can increase the risk of injury to a patient by creating a high friction area.

Another known method of marking low friction coated medical devices is to print ink or otherwise deposit ink or paint on the surface of the coating. However, low friction coatings resist bonding with inks, and inks printed on low friction coatings may peel off and be left inside the patient's body, which may harm the patient. Ink may also rub or peel off before or during use of the medical device, thus destroying the usefulness of the markings, and increasing the risk that the medical device will be inserted either too deep, or not deep enough (and harm the patient and/or render the medical procedure ineffective). Furthermore, many medical devices have small diameters such that even thin layers of ink can significantly increase the diameter of the device, which, as previously described, is undesirable.

Marking low friction coated medical guide wires poses additional problems. Medical guide wires are generally shaped like coiled springs, having an elongated strand of medical wire helically wound such that adjacent turns of the wire are in contact with each other. Known methods of marking low friction coated medical guide wires, such as grinding or ablating the coating to expose the surface of the medical guide wire each have the disadvantages of either increasing or decreasing the diameter of the medical guide wire and/or removing the low friction coating, which is undesirable. Removal of the coating by mechanical processes such as by grinding or using abrasives could possibly weaken the thin wire that forms the coils of the medical guide wire. Laser ablation does not harm the wire, however it removes the low friction coating which is undesirable. Additionally, despite repeated rinsing, material removed from the coating can get caught between the turns or adjacent segments of the medical wire and can be deposited in a patient's body during a medical procedure, which could be potentially harmful or even fatal for the patient. Furthermore, marking the coated medical guide wire with paint is not effective because paint will easily crack and delaminate between adjacent turns of the medical guide wire and the paint could be deposited in a patient's body, which could also be harmful and potentially fatal for the patient.

One known method of forming a low-friction coating on a medical device includes applying an aqueous PTFE solution to the surface of a medical device. The solution includes particles of a low friction material such as PTFE, an acid such as chromic acid, a pigment, wetting agents, other ingredients, and distilled water. The solution is cured at a high temperature such as 750° F. (399° C.) to cure the coating and permanently adhere the coating to the substrate. The pigments used in this method are generally stable at temperatures exceeding the cure temperature so that they do not shift color during the curing process. Although the pigments used in this method generally will shift color at temperatures above the cure temperature, when heated to such temperatures the low friction characteristic of the PTFE coating permanently degrades and the bonds between the low friction coating and the medical device weaken, which destroys the coating adhesion, properties and utility of the low friction coating.

Accordingly, a need exists for improved markings on medical devices, and specifically medical wires or tube type devices with low friction coatings. Such a need exists for medical devices with markings that do not significantly increase or decrease the diameter of the medical device, or significantly adversely affect the function of the low friction coating.

SUMMARY

The present disclosure relates in general to medical devices, and specifically to medical devices having low-friction (including low friction, low surface energy and/or non-stick) coatings having visible markings, and a method for manufacturing the same.

In one embodiment, the medical device, such as a medical wire, includes a coating applied to the surface of the medical device. The coating includes a base layer bonded to the surface of the medical device and an at least partially low-friction top coat on the surface of the coating. The base layer includes pigments that change to a different, contrasting color when heated above a discoloration or color shifting temperature, or are otherwise stimulated by suitable stimulants. In one embodiment, the color of the pigment in one area contrasts with the color of the pigment in an adjacent area without otherwise affecting, degrading, deteriorating, compromising or changing the chemical composition of the low-friction coating and/or significantly affecting, degrading, deteriorating, compromising or changing one or more characteristics, functions, or properties of the low-friction coating. The areas of different color created in locations along the length of the low-friction coated medical device form markings which enable a surgeon or other medical professional to determine the length of the medical device inserted into a body by observing the markings on the portion of the device located exterior to the body.

In one embodiment, a coating is applied to the surface of a medical device, such as a medical wire. The coating includes a binder, at least one heat-sensitive pigment, at least one relatively heat-stable pigment and particles of a low-friction material such as PTFE. The medical device and the applied coating are then heated above a designated temperature, such as 500° F. (260° C.) to cure the coating. The binder and heat sensitive pigment used in this method are generally stable at the cure temperature, but one or both will discolor or shift color at temperatures above a specific temperature greater than 500° F. (260° C.). During the initial curing process, the low-friction particles soften and at least some of the low-friction material migrates or flows to the surface of the coating due to the different rates of curing of the low-friction particles and the binder. At or near the surface of the coating, the low-friction material fuses or glazes over the base layer to create a smooth, substantially continuous top coat comprised of low-friction material. Also during the curing process, the binder material binds with the surface of the medical device and the heat activated pigment is left interspersed within the binder material. When curing is complete, the medical device includes a base layer including a binder material and a heat activated pigment, and an at least partially transparent top coat substantially comprised of low friction or low surface energy materials. One advantage of this method over the aqueous solution method of applying a coating is that the coating in this method is cured at a lower temperature, which enables the heat sensitive pigment to be formulated to shift color at a lower temperature. The lower color shifting temperature enables the color of the heat sensitive pigment (which is under the outer, relatively transparent low-friction coating) to shift without substantially affecting, degrading, deteriorating, compromising or changing the chemical composition of the low-friction material of the coating and/or affecting, degrading, deteriorating, compromising or changing one or more characteristics, functions, or properties of the low-friction material of the coating. The lower color shifting temperature also enables the color of the pigment to shift without substantially affecting, degrading, deteriorating, compromising or changing one or more characteristics, properties, or functions of the adherence of the coating to the surface of the medical device.

After initially curing of the specific coating on the surface of the medical device, markings in the coating are created by selectively heating portions of the coating, including the heat activated pigment, above a color shifting temperature, or by selectively stimulating portions of the coating by using a suitable external stimulant. The color shifting temperature must be greater than the curing temperature, so that the pigment does not shift or change color during the curing process. The color shifting temperature must also be less than the temperatures at which either the binder material significantly loses its adhesion to the surface of the medical device, or the low-friction material of the coating substantially degrades. That is, if the color shifting temperature is too high, then the low-friction character of the top coat will degrade (nullifying the effectiveness of the low-friction coating), and the binder material will lose adhesion to the surface of the medical device (causing the coating to deteriorate, delaminate or peel off) before the pigment can be heated above the color shifting temperature. A proper color shifting temperature enables areas of different or contrasting color to be created after curing and without adversely affecting the low-friction character of the top coat or the adhesion of the base layer to the surface of the medical device. Therefore, a proper color shifting temperature enables contrasting color markings to be created on the medical device without adversely affecting the function of the medical device or the coating thereon.

In one embodiment, a first area of the low-friction coating is heated to the color shifting temperature to shift or change the color of the heat activated pigment for a specific distance, such as 3 mm as measured from the distal end, proximal end or from the center of the medical device. In this embodiment, a distance, such as 10 mm, is then measured from the first area to a second area. The second area, such as an area of 3 mm in length, is subsequently heated to the color shifting temperature to shift or change the color of the heat activated pigment. Such heatings to create areas of shifted color, when repeated in any sequence along the length of the device, result in specific length markings at measured intervals. The markings of such width, depth or distance marked medical devices enable surgeons or other medical professionals to determine, based on a predetermined pattern known to the device user, the length of the medical device inserted into a patient, whether from the proximal or distal end. Accordingly, the medical device and method disclosed herein provide the advantages of having specific markings that do not significantly increase or decrease the diameter of the medical device, or significantly adversely affect the function of the low-friction coating and further provide a coating over the base material of the medical wire or device.

In one embodiment, a coating is applied to the surface of a medical wire. The medical wire is generally elongated and has a proximal end, a distal end, and at least one surface. The medical wire or device is made of steel, stainless steel, aluminum, Nitinol, titanium, copper, plastic, ceramic, rubber, synthetic rubber or any other suitable material. The coating applied to the surface of the medical wire includes a binder resin (such as an epoxy, polyimide, polyetheretherketone (PEEK), polyetherketone (PEK), polyamide, PTFE or polyarylsulfone), and one or more suitable pigments, such as any suitable heat activated pigment, organic pigment, inorganic pigment, extender pigment, magnetic receptive pigment, and/or laser receptive and excitable pigment. The coating also includes particles of a low friction and/or low surface energy material such as PTFE, fluorinated ethylene propylene (FEP), polyethylene (PE), perfluoroalkoxy (PFA) or any low surface energy particulate material. The coating is applied to the surface of the medical device and is adhered to the surface of the medical device by being cured by heating the coating to a designated temperature and for a designated period of time to cure the binder resin. During the curing process, particles of the binder resin crosslink, sinter, or form bonds with other particles of the binder resin and the substrate. The specially formulated binder resin also forms bonds with the surface of the medical device. Also during the curing process, some of the low-friction material migrates or flows to the surface of the coating and fuses together to form a substantially continuous glaze or top coat or outer surface of low-friction material.

In one embodiment, after the coating is cured, portions of the heat activated pigment are heated above the color shifting temperature. In one embodiment, heat is selectively applied to a portion of the top coat, which subsequently heats the base layer underneath the clear top layer. In one embodiment, infrared or laser heat is applied to the base layer by passing the radiated heat through the at least partially transparent top layer. In one embodiment, the medical device is heated by induction and the base layer is heated by conduction from one or more designated portions of the heated coated medical device.

When the base layer is heated to a temperature above the color shifting temperature, the heat activated pigment changes color from a first color to a second different color. The color of the pigment (within the matrix of the coating) is shifted in selected locations along the length of the device such that the different colors serve as visual indicia which indicate a designated marking that may denote length of the medical device or a designated position on the medical device. Using a jet of hot air, open flame, plasma heat or other suitable mechanism or apparatus for applying heat, the color of a small length of the medical wire in a first location is shifted such that the wire has a thin, 2 mm long for example, band of different color around its circumference. A distance, such as 10 cm, is then measured from the first location having a different color to a second location along the length of the device. The second location is also selectively heated and caused to shift color such that the wire has a second 2 mm long band of a different color. In this manner, repeated locations of shifted color along the length of the device indicate to surgeons or other medical professionals the length of the medical wire that is inserted into a patient.

It should be appreciated that the locations of shifted color can be created in any suitable combination of lengths and patterns to indicate different lengths and locations on the medical device. For example, a single mark of 5 mm indicates a location in the exact center of a guide wire. In another example, a pattern of bands can provide a distance marker from the distal end of a medical device. For example, from the exact center of a guide wire toward the distal end, 5 mm marks are provided as a single mark 10 mm from the centerline, another 2 mm mark is provided at 15 mm from the centerline, two bands of 5 mm spaced by 1 cm are provided at 20 mm from the centerline, another band of 2 mm is provided at 25 mm from the centerline followed by three 5 mm bands at 30 mm from the centerline, and so on to the distal end of the device. In another example, a medical device disclosed herein includes a first shifted color (which runs from a distal end of the medical device to a halfway or middle point of the medical device) and a second, contrasting color (which runs from the proximal end of the medical device to the halfway or middle point of the medical device). Such a configuration provides that a surgeon or medical professional can quickly identify when more than 50% of the medical device is internal to the patient and determine whether a different medical device of a different length should be employed. Such a configuration can also assist the surgeon or medical practitioner in determining the length of a catheter or other device which will subsequently be placed over the guide wire to a specified distance, based on the markings on the exposed guide wire. Another mid-point marking system can be a series of 2, 3, 4 and 5 mm marks preceding (and optionally succeeding) a centerline mark of two 5 cm marks spaced apart by 1 cm, which denotes the exact centerline of the device. Such a marking system provides the surgeon a warning with the narrower pattern of marks that the centerline is being approached. Accordingly, many marking codes or patterns can be used denoting distance from the distal end of the medical device, the proximal end of the medical device, the centerline of the medical device or any suitable point or location of the medical device required by the medical device manufacturer.

In one alternative embodiment, a radiopaque material or compound, such as barium sulfide, barium sulfate or a suitable metal, such as tungsten, is added to the coating. In this embodiment, a suitable marking is provided or shows up using a suitable imaging device, such as an x-ray device, a magnetic resonance imaging (MRI) device, or an ultrasound device. In one such embodiment, the imaging device displays an image of the radiopaque marking on one or more display devices of the imaging device. In another such embodiment, the imaging device produces an image of the radiopaque marking on a film or other suitable media, such as by producing an x-ray film. In these embodiments, the surgeon or other medical professional utilize the imaging device to determine an exact location of the medical device inside a patient and/or to determine one or more measurements inside the patient.

In another embodiment, a base layer including a radiopaque material is selectively bonded to a surface of the otherwise uncoated medical device. For example, the radiopaque material is bonded to different areas of the medical device to form discrete bands of the radiopaque material. In this embodiment, a suitable amount or density of the radiopaque material is selectively bonded to the surface of the medical device such that the radiopaque material is detectable when the medical device is viewed using a suitable imaging device. After selectively bonding the radiopaque material to a surface of the medical device, the base layer coated medical device (which includes the radiopaque material) is heated above a first designated temperature to cure the base layer. After curing the medical device and the applied base layer, a low-friction material, such as PTFE, is applied to the base layer coated surfaces of the medical device and the uncoated surfaces of the medical device. The coated medical device and the low-friction material are then heated above a second designated temperature to cure the coating of the low-friction material. Thus, the medical device of this embodiment includes a plurality of discrete markings of a radiopaque material covered by a low-friction top coating. Accordingly, the resulting medical device will have different slightly elevated areas or bands along the length of the medical device (such as to indicate distance), have low-friction characteristics (including low friction, low surface energy and/or non-stick characteristics) and include markings that show up using an imaging device, such as an x-ray device or on an x-ray film, to provide an exact location of the medical device inside a patient for safety and/or measurement purposes.

In another embodiment, a base layer including a low-friction material, such as PTFE, is applied to a surface of the medical device. The medical device and the applied base layer are then heated above a first designated temperature to cure the coating. After curing the medical device and the applied base layer, a radiopaque material is selectively bonded to specified surface areas of the coated medical device. The coated medical device and the applied radiopaque material are then heated above a second designated temperature to cure the radiopaque material. For example, the radiopaque material is bonded to different areas of the medical device to form discrete bands of the radiopaque material. In this example embodiment, a suitable amount or density of the radiopaque material is selectively bonded to the surface of the coated medical device such that the radiopaque material is detectable when the medical device is viewed using a suitable imaging device. Thus, the medical device of this embodiment includes a plurality of discrete markings of a radiopaque material above or otherwise bonded to a low-friction coating. Accordingly, the resulting medical device will have different elevated bands or areas along the length of the medical device (such as to indicate distance), have low-friction characteristics (including low friction, low surface energy and/or non-stick characteristics) and include markings that show up using a suitable imaging device, such as an x-ray device or on an x-ray film, to provide an exact location of the medical device inside a patient for safety and/or measurement purposes.

In another embodiment, as described above, certain areas of the medical device are marked using color shifting pigments and radiopaque materials are applied to certain other areas of the medical device. In one such embodiment, a suitable radiopaque material is applied to a first portion of a medical wire that is inserted into a patient and a second portion of the medical wire that is not inserted into the patient is marked using the above-described color shifting pigments. In this embodiment, a surgeon or other medical professional can utilize: (1) the portion of the medical wire that is inserted into the patient and a suitable imaging device, and (2) the visibly marked portion of the medical wire not inserted inside the patient to determine the length of the medical wire inserted into a patient's body, the length of certain elements inside a patient, and the exact location of certain elements inside a patient.

In another embodiment, a first or base low-friction layer, including a low-friction material, such as PTFE, is applied to a surface of the medical device and suitably cured. In one such embodiment, the first low-friction layer includes a first relatively light colored pigment, such as a white colored pigment. After applying the first low-friction layer, a relatively thin (as compared to the first or base low-friction layer) second low-friction layer, including a low-friction material, such as PTFE, is applied to the coated surface of the medical device and suitably cured to bond the two layers together. In one such embodiment, the second low-friction layer includes a second relatively dark colored pigment, such as a green, black or blue colored pigment. In another such embodiment, the second low-friction layer also includes one or more laser receptive pigments.

After applying the two low-friction layers of contrasting color, a suitable laser and laser energy is selectively applied to different areas of the coated medical device. In this embodiment, the laser ablates or removes the relatively thin outer second low-friction layer while not adversely affecting the first low-friction layer. That is, the second low-friction layer with the relatively dark colored pigment (and optionally the additional laser receptive pigments) absorbs the energy (or more of the energy) of the laser and is accordingly vaporized or ablated from the coated surface of the medical device, while the first low-friction layer with a relatively light colored pigment does not absorb the energy of the laser and is thus not affected by (or is not significantly affected by) the applied laser energy. After the laser energy is selectively applied to different areas of the medical device, the resulting outer surfaces of the laser applied areas of the medical device will include the first low-friction, light colored coating and the outer surfaces of the non-laser applied areas of the medical device will include the second low-friction dark colored coating. It should be appreciated that since a thin layer of the dark colored low-friction material is applied to the medical device, when that thin layer is removed from the medical device, any diametrical reductions of the diameter of the surface of the low-friction coating will be relatively shallow and not create any substantially sharp edged shoulders which can scrape bodily tissues, snag vessels or arteries of the patient, or otherwise cause damage and/or trauma to virtually any part of the patient's body. It should be appreciated that the laser energy which creates the ablation of the second or outer low-friction layer can be reduced along and nearest the edges or margins of the ablated area to create a tapering effect (i.e., a smoothening of the diametrical transition) thus reducing the tactile feeling of a "notch" between the two layers of different colored coatings. Accordingly, in this embodiment, different areas of the coated medical device are suitably marked with different colors and the medical device includes at least one suitable low-friction coating applied to the outer surface of the medical device such that the low-friction surface is always in contact with the counter face or the tissue of the patient. As described above, such different colored areas along the surface of the low surface energy, low-friction coated medical device provide a coated medical device (without any unintentionally exposed metal portions) configured to indicate to surgeons or other medical professionals the length of the medical device that is inserted into a patient.

It is therefore an advantage of the medical device and method disclosed herein to provide a marked low-friction coated medical device having markings which do not affect the function or form of the low-friction coating and enable a surgeon or other medical professional to determine the length of a medical device inserted into a patient's body, and to modulate the speed at which the medical device is being inserted or extracted from the patient's body. Such coated medical device provides no dynamic restrictions to any predetermined or required modulation of speed due to the removal or interruption of the low-friction coating to the smooth, low-friction outer surface of the device. The medical device and method disclosed herein further provides a marked medical device with a smooth, continuous low-friction surface with a substantially constant diameter which prevents the medical device from snagging, sticking, tearing, or otherwise damaging vessels, arteries, or other tissues of a patient during insertion, positioning, and extraction of the medical device. The low-friction coating is marked without otherwise affecting, degrading, deteriorating, changing the chemical composition of, changing one or more characteristics, functions, or properties of or removing in the entirety, the low-friction coating. The marked low-friction coated medical device disclosed herein enables a surgeon or other medical professional to smoothly, easily, accurately, and safely insert and position the medical device in a patients body during a medical procedure and know what distance is inserted into the patient's body and what distance remains outside of the patient's body. The medical device and method disclosed herein further provides a marked medical device with different slightly elevated bands or areas along the length of the medical device (such as to indicate distance), have low-friction characteristics (including low friction, low surface energy and/or non-stick characteristics) and include markings that show up using a suitable imaging device, such as an x-ray device or on an x-ray film, to provide an exact location of the medical device inside a patient for safety and/or measurement purposes.

Additional features and advantages are described herein, and will be apparent from, the following Detailed Description and the figures.

BRIEF DESCRIPTION OF THE FIGURES

FIG. 1 is a flow chart describing one embodiment of the disclosed method of coating and marking a medical device.

FIG. 2 is a side view of one embodiment of a segment of an uncoated medical device disclosed herein.

FIG. 3 is a side view, partially in section, of the medical device of FIG. 2 including an uncured coating applied to the surface thereof.

FIG. 4 is a side view, partially in section, of the medical device of FIG. 3 after the coating is cured.

DETAILED DESCRIPTION

Figure 5:
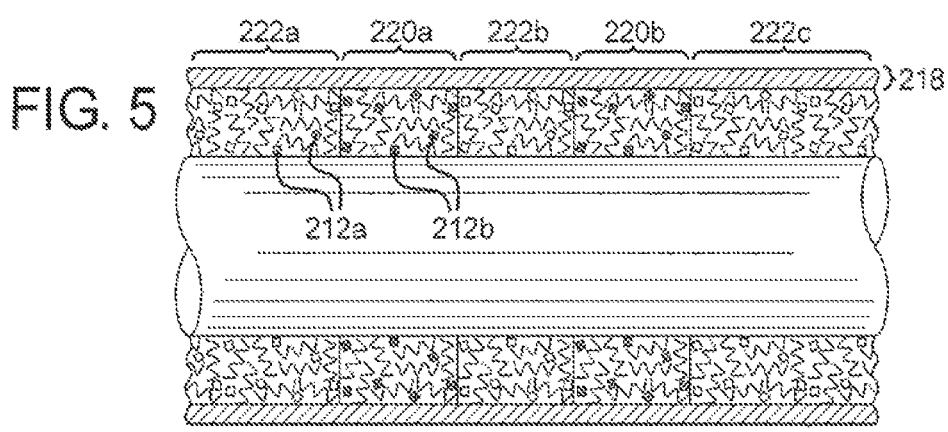
FIG. 5 is a side view, partially in section, of the coated medical device of FIG. 4 including markings resulting from shifting the color of selected areas of the base layer of the coating.

For the purposes of this application only, the medical device is referred to and illustrated as a medical wire or a medical guide wire. However, the medical device disclosed herein is any device that is inserted into a patient or connects to a device that inserts a device into a patient in connection with any medical procedure. Such medical devices include, but are not limited to medical wires, medical guide wires, catheters, needles, soft tissue needles, biopsy devices, biopsy tubular sampling devices, soft tissue biopsy devices, soft tissue tubular devices, hook-type biopsy devices, cannulas, probes, electrosurgical electrodes, blades and knives. The medical device is constructed from any suitable material, including but not limited to metals such as steel (both high- and low-carbon content), stainless steel, aluminum, titanium, copper, nickel, silver, nitinol, and other metals and metal alloys. Other suitable materials of which a medical device may be constructed include ceramics, rubber, any suitable polymer material and any suitable plastic, including but not limited to nylon, polyetheretherketone (PEEK), polyetherketone (PEK), polyphenylenesulphide (PPS), acrylonitrile-butadiene-styrene (ABS), polycarbonate, epoxy, polyester, and phenolic, or any combination thereof. It should be appreciated that various changes and modifications to the presently preferred embodiments described herein will be apparent to those skilled in the art. Such changes and modifications can be made without departing from the spirit and scope of the present subject matter and without diminishing its intended advantages.

In one embodiment, the medical device illustrated in FIG. 2. is an medical wire before having a coating applied thereto. The medical wire 200 is generally elongated and has a proximal end 202, a distal end 204, and an outer surface 206. In one embodiment, the medical device is a medical guide wire, wherein the guide wire includes one or more elongated strands of coated medical wire helically wound such that adjacent turns of the wire are in contact with each other. The resulting medical guide wire is generally shaped like a coiled spring and includes a proximal end and a distal end.

In one embodiment, referring to FIG. 1, before applying a coating to the surface of the medical device, in this case a medical wire, the medical wire is prepared for coating as indicated in block 100 of FIG. 1. In one such embodiment, the medical wire is cleaned with a cleaner to remove impurities which are present on the surface of the medical wire. Impurities such as oils may impede bonding of a coating to the surface of the medical wire, and also may cause damage to a patient if inserted into a patient's body during a medical procedure. The cleaner, such as a solvent, acid solution or alkaline, is suitably applied, such as manually applied, mechanically applied or ultrasonically applied to the medical wire. In another embodiment, the medical wire is cleaned by condensing a vaporized cleaner on the surface of the medical wire, wherein the cleaner dissolves and washes away the oils on the surface of the medical wire. In another embodiment, laser energy from a laser device, such as a YAG laser, is directed at the surface of the medical wire to clean the surface of the medical wire.

In another embodiment, grit blasting, tumble blasting, or sandblasting with a medium such as aluminum oxide, garnet, or silicone carbide is used to clean the surface of the medical wire and create a roughened surface which promotes bonding with a coating. In another embodiment, the surface of the medical wire is etched with acid or alkaline to clean and roughen the surface of the medical wire. In another embodiment, laser energy from a laser device, such as a YAG laser, is directed at the surface of the medical wire. In this embodiment, the laser device provides sufficient energy to roughen the outer surface of the smooth medical wire resulting in a textured, matte, or generally non-smooth surface to the medical wire. Such a non-smooth surface promotes adhesion of subsequently applied coatings, without the abrasive dust produced by mechanical abrasion.

In another embodiment, the medical wire is cleaned with an ultrasonic cleaner used in combination, prior or after the ultrasonic degreaser, with a solvent such as acetone, alcohol or another degreaser. Alternatively, the medical wire is pre-cleaned or the method is performed in a "clean room" where the cleaned part is manufactured and the step is not necessary. In another embodiment, the medical wire is heated to a temperature, depending on the metal alloy or other material of the medical wire, in excess of at least 700° F. (371° C.) for a period of time sufficient to thermally degrade surface impurities, draw oils and other impurities out of any pores in the surface of the medical wire and create a non-acidic "passivation" of the surface of the medical wire. In another embodiment, the medical wire is cleaned in a batch or bulk cleaning method, thereby cleaning all of the surfaces of the medical wire. In another embodiment, the medical wire is heated before applying a coating to reduce ambient moisture on the surface of the medical wire and improve adhesion of a coating to the medical wire. In another embodiment, the medical wire is cleaned with a grit-blasting system which includes several grit-blasting nozzles cleaning the surface of the medical wire with relatively high velocity particles of an abrasive such as aluminum oxide or silicon carbide. In other embodiments, any combination of the cleaning methods mentioned above are used to improve the cleaning process and promote adhesion of a coating to the medical wire.

After preparing the medical wire for coating, a coating is applied to one or more surfaces of the medical wire as indicated in block 102 of FIG. 1. Referring to FIG. 3, the coating 208 includes a binder 210a, such as an epoxy, phenolic, phenoxy, polyimide, polyamide, polyamide-amide, polyphenylene sulfide, polyarylsulfone, polyethylene, polytetrafluoroethylene, fluorinated ethylene propylene, perfluoroalkoxy, polyetheretherketone (PEEK), polyetherketone (PEK), or any suitable binder or resin. Such suitable binders include any binder which, when cured, adheres to the surface of the medical device, and is flexible, stable, resistant to chemicals, and/ or is readily sterilized and resistant to contamination. In one embodiment, the coating includes an ultraviolet light cure resin to semi or fully cure the coating. In another embodiment, the coating includes an electron beam cure resin.

The coating also includes at least one pigment 212a such as any suitable organic pigment, inorganic pigment, extender pigment, magnetic receptive pigment and/or laser excitable pigments. The organic pigments (with low to moderate heat resistance and which are represented as bright colors) include, but are not limited to, phthalocyanine blues and greens, diarylide yellows and oranges, quanacridone, naphthol and toluidine reds, carbizole violets, and carbon black. The inorganic pigments (with moderate to high temperature resistance and which are represented as dull to moderately bright colors) include, but are not limited to, iron oxide reds and yellows, chrome oxide greens, titanium oxide white, cadmium reds, ultramarine blues, moly oranges, lead chromate yellows, and mixed metal oxides of various shades of brown, yellow, blue, green and black. The extender pigments (which are inorganic and provide a reinforcing/strengthening function) include, but are not limited to, talc, calcium carbonate, silicate and sulfate, silica, mica, aluminum hydrate and silicate, and barium sulfate (blanc fixe/barites). The laser exciteable pigments (which are excited by laser energy), such as near-infrared reflective pigements include, but are not limited to, mica, pearl pigment, Kaolin and aluminum silicate derivatives, antomony trioxide, metallic pigment, aluminum flake pigment, and iron oxide. Additionally, the coating may also include one or more of the following functional pigments, such as conductive pigments, flattening pigments for controlling gloss, clays and other rheology modifying pigments.

In one embodiment, a coating which is formulated with magnetic receptive pigments and/or electromagnetic receptive pigments is utilized, wherein these magnetic receptive pigments will provide internal heat when subjected to one or more appropriate magnetic fields or electromagnetic fields. In this embodiment, such magnetic receptive pigments are applied to non-magnetic substrates, such as non-magnetic stainless steel, ceramics, plastic or polymers. Such magnetic receptive pigments are formulated with low-friction materials and appropriate color pigments and binders, such as epoxy and polyimide, which when cured at a suitable temperature provides adhesion to the substrate and also creates the low-friction surface. In this embodiment, the medical device is subsequently internally heated by exciting or energizing the dispersed magnetic receptive particles, which causes select areas of the medical device to change colors from the primary color to a darker color in the areas where the coated device is selectively subjected to the magnetic forces, while not overheating either the binder resin or the outer layer of low-friction material.

The pigment is configured to change color when heated above a color shifting temperature. The color shifting temperature is greater than, such as by 50-100° F. (10-38° C.), the designated temperature at which the coating is cured to allow the coating to be cured without changing the color of the pigment during the curing process. The color shifting temperature of the heat activated pigment should also be lower than the temperatures at which either the low-friction characteristics of the low-friction material, or the adhesive characteristics of the binder resin, are substantially affected, degraded, or deteriorated, or the chemical composition, characteristics, functions, or properties of the low-friction coating and/or base resin are changed.

The coating also includes particles of a low-friction material 214a such as PTFE or PE. After curing, the low-friction material forms an at least partially transparent top coat such that at least some visible light passes through the low-friction material. In one embodiment, the particles are micron- and/or sub-micron-sized. In another embodiment, the low-friction material is resistant to chemicals such that the low-friction material will provide a low surface energy outer layer and will resist corrosion, resist oxidization, resist breaking down, resist forming bonds with other materials, and otherwise be unaffected by contacting other chemicals. In another embodiment, the low-friction material is pure and free of contaminants such that the low-friction material can safely be used in medical procedures and can safely contact food for human consumption. In another embodiment, the low-friction material is irradiated, prior to incorporation in the coating, with an electron beam (or other suitable energy source) so that the resulting particles create an easily wetted surface which enables better adhesion to the binder material.

In another embodiment, the coating includes additives, such as silane coupling agents, other materials formulated to improve the bonding capabilities of a coating to the surface of the medical wire, particularly smooth surfaces, or other materials which modify the curing characteristics or the drying characteristics of the coating before curing. In another embodiment, the coating includes additives to improve the wear characteristics, corrosion resistance, and/or electrical properties of the coating. For example, in one embodiment, the uncured coating includes approximately 30%-50% by volume of a base resin, 1%-30% of a heat stable pigment, and 0.5%-15% of a pigment that shifts from a first color to a second, contrasting color when heated from a first temperature to a second temperature which is 20-200° F. (11-93° C.) higher than the first temperature. The uncured coating also includes 2%-10% by volume of low-friction particles and trace amounts of a wetting agent, a silane coupling agent, a hardening agent, and/or curing or drying agents. In another embodiment, an alcohol (or other suitable solvent) and a silane coupling agent (or other suitable adhesion promoting agent) are utilized as a primer dip on the smooth or semi-smooth surface of the medical device. For example, a dilute mixture of 2-3% silane in alcohol is applied to the medical device prior to the application of any suitable top coats followed by an appropriate curing procedure to bond the silane to the surface of the coated medical device to promote adhesion of any subsequently applied top coats.

In one embodiment, a coating is applied by spraying the surface of a medical wire with the coating. In one embodiment, the coating is sprayed on, applied using a air atomizer or appropriate atomizing device, applied by a siphon, gravity, ultrasonic or pressure pot method which forces the coating through a nozzle at high pressure such that the coating forms a vapor or mist which is directed toward the surface of the medical wire. In another embodiment, the coating is applied with a variation of siphon or gravity spraying wherein the coating is sprayed at a lower pressure and in higher volume to reduce the amount of volatile organic compounds released during the spraying process. In another embodiment, a medical wire device is dipped into a reservoir filled with the coating. Once submerged, the medical device or wire is removed from the reservoir and "spun" or rapidly rotated to remove excess coating by centrifugal force. In another embodiment, a medical device or wire is "tumbled" in a rotating barrel or other rotating enclosure including a coating. Not air is blown over the tumbling medical wire to at least partially cure the coating as it is applied to the medical wire. In another embodiment, high speed rollers are used to apply a film of coating to the surface of a medical wire. In another embodiment, a medical wire is passed under a falling curtain of the coating to coat the surface of the medical wire. In another embodiment, an electrical current is passed thru an aqueous bath containing the appropriate particles and such particles are adhered to the medical wire using positive and negative differentials in voltage between the bath of particles and the medical wire. In this embodiment, such deposition is regulated by the combination of electrical energy and the chemistry of the bath containing the particles and resins and agents that provide the proper characteristics once cured to the medical device.

In another embodiment, a powder coating system is employed. This powder coating system includes a primer, where required, of a liquid that is preapplied and either cured to dry or remains wet prior to the application of a topcoat of a powder. In this embodiment, the powder may include a low-friction material such as PFA, FEP, PTFE, PE, PEEK, PEK or appropriate low-friction particles or a combination of the above plus appropriate pigments similar to those described in the liquid-type coatings described above.

In another embodiment, an electrostatic, tribo-charged or opposite electrostatic charged spray or powder spray method is used to apply the coating to a medical wire. The electrostatically charged spray enables an operator to better control the application uniformity of the coating and thereby enhances the uniformity, density and application of the coating on the surface of the medical wire. It should be appreciated that the coating may have one or more characteristics altered to allow for more efficient electrostatic, tribo-charged or opposite electrostatic charged spray techniques to be used to apply the coating to a medical wire.

Moreover, the above-described "tribo-charge", or electrically charged as with conventional electrostatic application technique alters the edge coverage thickness of the applied coating based on any design requirements which require a more uniformly applied coating to all surfaces of the medical wire, whether the configuration has sharp or round edges. This technique results in greater coating transfer efficiency while also optimizing the different edge coverage thicknesses of the applied coating, whether the medical device is a medical wire, medical guide wire, catheter, needle, knife, cannula, probe, or other medical device.

Referring to FIG. 3, one embodiment of the medical wire is illustrated wherein the medical wire includes an uncured coating 210 applied to its surface. After the coating is applied to the surface of the medical wire, the coating is cured as indicated in block 104 of FIG. 1 to harden the coating and strengthen the bond between the coating and the medical wire, thereby curing the coating. The curing process is performed by heating the coating at a predetermined temperature or temperatures for a predetermined length or lengths of time, air-drying the coating at ambient temperature, or by utilizing any suitable internal or external curing process. It should be appreciated that curing may be accomplished by exposure to light from an infrared, visible, or ultraviolet light source.

In one embodiment, as illustrated in FIG. 4, during the curing process, the molecules of a binder, such as an epoxy 210a crosslink and form chemical bonds with each other, and bond with the surface of the medical wire. The crosslinked epoxy molecules form an epoxy matrix 216 including crosslinked binder molecules, one or more low-friction materials, one or more pigments, and one or more other ingredients such as wetting agents, coupling agents, hardening agents, and/or other additives. Also during the curing process, the particles of low-friction material such as PTFE 214b soften and at least some of the PTFE or other low-friction material is squeezed out or displaced from the epoxy matrix and migrates, rises, or flows to the surface of the coating. At or near the surface of the coating, the PTFE molecules bond or fuse together to form a thin, partially transparent top coat 218 of PTFE on the outer surface of the coating. When the curing process is complete, as illustrated in FIG. 5, the coating includes a base layer including the epoxy matrix, and a top coat including fused molecules of PTFE. It should be appreciated that when the coating is cured, the epoxy matrix exhibits a first color, such as light blue, which is visible through the at least partially transparent PTFE top coat. Also, the surface of the coating 212 is smooth and resists sticking to other objects, which enables a surgeon or other medical professional to gently, smoothly, and accurately insert one end of the coated medical wire 220 into a patient's body.

Figure 6:
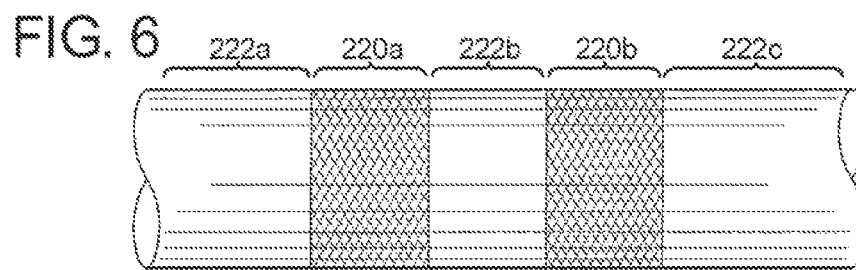
FIG. 6 is a side view of the coated medical device of FIG. 5.

Referring now to FIG. 5 and FIG. 6, in one embodiment, after curing the applied coating to harden the coating and form a low-friction top coat, markings 220a and 220b are created on the coated medical device or wire as indicated in Block 106 of FIG. 1. The markings are created by selectively heating portions of the coating above a color shifting temperature while simultaneously maintaining adjacent portions 222a, 220b, and 220c at a cooler temperature (with a suitable masking device). When heated above the color shifting temperature, the pigment in the selectively heated portions changes from a first color to a second color. For example, in one embodiment, as illustrated in FIG. 5, the coating applied to the medical wire is generally light blue in color. However, at measured intervals along the length of the medical wire, short sections of the base layer of the coating are dark brown or black (i.e., contrasting) in color. Thus, a first segment such as a 100 mm long segment of the coated medical wire is light blue in color. A second adjacent segment such as a 3 cm long segment of the coated medical wire is dark brown in color, and a third segment such as a 50 mm long segment, adjacent to the second segment, is light blue in color. The pattern of alternating light blue and dark brown or black segments is repeated from the proximal end to the distal end of the coated medical wire, resulting in a coated medical wire having markings which visually indicate each 50 mm of length of the coated medical wire. It should be appreciated that the color transitions of the coated medical device may be absolute (i.e., a first color ends and a second, contrasting color begins) or gradual or feathered (i.e., a first color bleeds into a second, transitioning color which bleeds into a third color which contrasts with the first color). The markings enable a surgeon or other medical professional to determine the length of the coated medical wire inserted into a patient's body (or the length of the coated medical wire remaining outside the patient's body) during a medical procedure.

Figure 7:
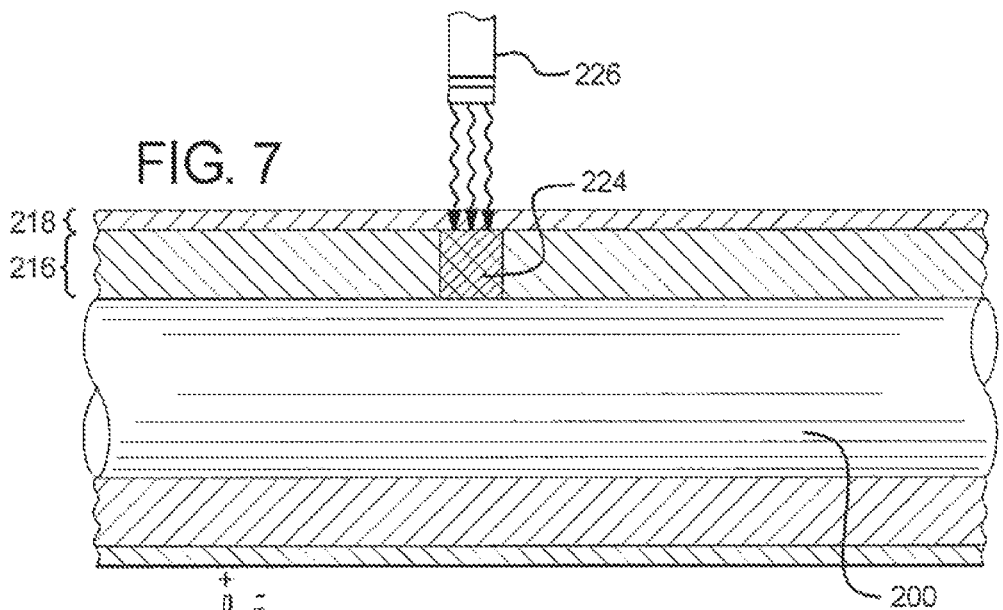
FIG. 7 is a side view, partially in section, of the coated medical device of FIGS. 5 to 6, including a laser for heating portions of the coating of the coated medical device.

Referring to FIG. 7, in one or more embodiments, the pigment in the coating is heated above the color shifting temperature by radiated heat. Radiated heat is applied from any radiant source, such as hot air, open flame, heated filaments, or lasers 226. Radiated heat can be directed to specific portions of the coating by masking portions of the coating (with a suitable masking device) that are not intended to be heated above the color shifting temperature. Masking is accomplished by any suitable mechanism configured to shield the coating from the heat source. In one embodiment, hot air is blown toward a specific portion of the coating through a nozzle or other apparatus of directing or funneling air. In another embodiment, heat is directly applied to the surface of the medical device such that intimate contact occurs between the heat source and the coated surface. In another embodiment, when radiated or infrared heat is directed to a portion 224 of the coating, the at least partially transparent top coat allows certain designated amounts of radiated or infrared heat to pass through the top coat to the base layer, which absorbs the heat. This method heats the base layer while simultaneously keeping the low-friction top coat at a slightly cooler temperature, which has the advantage of preserving the low-friction character of the top coat and maintains the at least partial transparency of the top coat.

Figure 8:
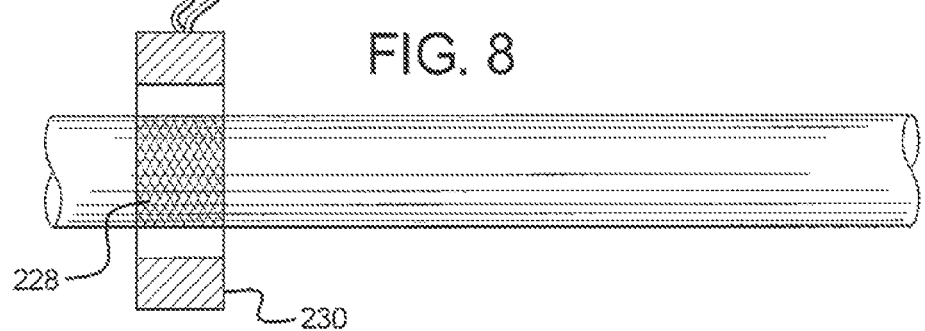
FIG. 8 is a side view of the coated medical device of FIGS. 5 to 6 including a magnetic induction coil for heating portions of the coated medical device.

Referring to FIG. 8, in one embodiment, the medical wire, which in this case is formed from a magnetic-type stainless or otherwise appropriate steel, is heated by magnetic induction wherein an induction coil 230 is energized with a frequency current, which imparts thermal energy in the medical wire. Electrical resistance in the medical wire causes electrical current energy to transform into heat energy. Heat from the medical wire then transfers to the base layer by thermal conduction, thus shifting the color of the portion of the base layer 228 above the heated segment of the medical wire. This method also has the advantage of keeping the low-friction top coat at a slightly cooler temperature, which preserves the low-friction character of the top coat. It should be appreciated that any suitable external energy source, such as flame heat, short wave infrared, medium wave infrared, hot air (electrically heated) with accurately placed orifices to make a specific and accurate marks on the medical wire, induction heat provided through a "bobby pin" or circular shaped coil and/or at right angles, and/or heat provided using induction energy may be used to stimulate the pigment and/or binder resin to cause the pigment and/or binder resin to be heated to shift color.

In different embodiments, radiation, microwaves, concentrated sound waves or other vibrations, or other external energy sources may also be used to selectively stimulate the pigment and/or binder resin to cause the pigment and/or binder resin to shift color. In another embodiment, laser energy, such as provided by a $CO_2$ (carbon dioxide), YAG lasers (Ytterbium), and fiber laser systems, provide the necessary energy to selectively stimulate the pigment and/or binder resin to cause the pigment, additive and/or binder resin to shift color. In this embodiment, these lasers have different depths of penetration, different "dot" sizes and/or different energy outputs which can be pulsed to selectively stimulate the pigment and/or binder resin to cause the pigment and/or binder resin to shift color.

In one embodiment, the medical device disclosed herein is coated, cured and selectively heated in sequential order. For example, a 180 mm long medical wire is entirely coated, entirely cured and then selectively heated exactly in the center to a width of 5 cm to cause the pigment and/or binder resin to shift color. In another embodiment, different portions of the medical device are coated, cured and selectively heated simultaneously. For example, a first 1 foot (30.4 cm) long portion of a 5 foot long (152.4 cm) medical wire is coated, while a second, different 1 foot (30.4 cm) long portion of the 5 foot (152.4 cm) long medical wire is cured, while a third, different 1 foot (30.4 cm) long portion of the 5 foot (152.4 cm) long medical wire is selectively heated to cause the pigment and/or binder resin to shift colors. In these embodiments, the medical device is coated in a suitable coater or utilizing a suitable coating device, the medical device is cured in a suitable curer or utilizing a suitable curing device and the medical device is selectively heated with a selective heater or utilizing a suitable selective heating device.

In one embodiment wherein the medical device is a medical guide wire generally having the shape of a coned spring, after the guide wire is formed, segments of the guide wire are selectively heated to shift the color of the heat activated pigment. The method of marking helically wound medical guide wire disclosed herein has the advantage of creating permanent markings at measured intervals along the length of the medical guide wire without weakening the medical guide wire, without creating debris or the potential for debris that could get caught between the adjacent coils of the medical guide wire, and without removing the low-friction coating or adversely affecting the function of the low-friction coating.

In another embodiment, a plurality of pigments having different color shifting temperatures are included in the coating. By selectively heating portions of the coating above the color shifting temperature of a first pigment but below the color shifting temperature of a second pigment, the color of the coating can be changed from a first color to a second different color. By selectively heating portions of the coating above the color shifting temperature of the second pigment, the color of the coating can be changed from the first color to a third different color. In one embodiment, for example, a coated medical wire includes a base color such as light blue, length markings in a second color, such as tan, and a second set of markings, such as a company logo, specifications, or use instructions in a third color such as brown or black.

Figure 9:
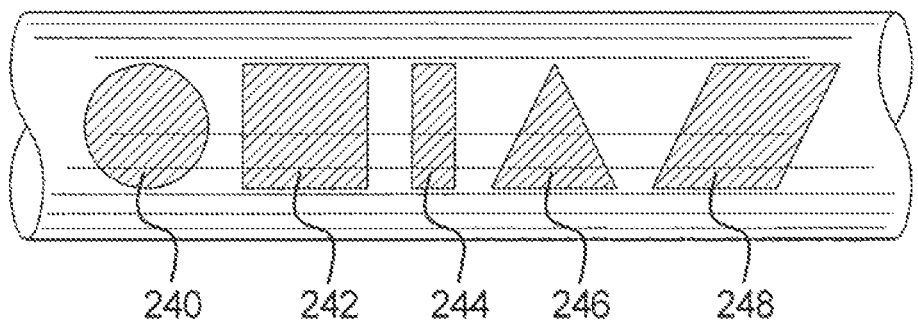
FIG. 9 is a side view of the coated medical device of FIGS. 5 to 6 including markings having geometric shapes.

In one embodiment, markings are created in the coating in any desired pattern or colors, or any combination of patterns and colors. In one such embodiment, the size of the markings and/or the number of marks grouped together to form a marking indicate different lengths of the marked medical device. In another such embodiment, small markings can be created at measured intervals along the length of the coated medical wire to indicate uniform length markers of the coated medical wire. In another embodiment, markings are created to indicate a specific distance from a reference point on the coated medical wire, such as a distance from the middle point, the proximal end and/or the distal end. For instance, one band having a shifted color can indicate a first distance from the distal end, while two bands having shifted colors in close proximity can indicate a second distance from the distal end. Likewise, in another embodiment, depending on the size and shape of the medical device, numbers or characters are created in the coating to indicate a distance from a middle point, the distal end and/or the proximal end. In another embodiment, as illustrated in FIG. 9, one or more geometric shapes, including but not limited to circles 240, squares 242, rectangles 244, triangles 246, parallelograms 248, and other polygrams are created in the coating to indicate lengths of the medical device.

Figure 10:
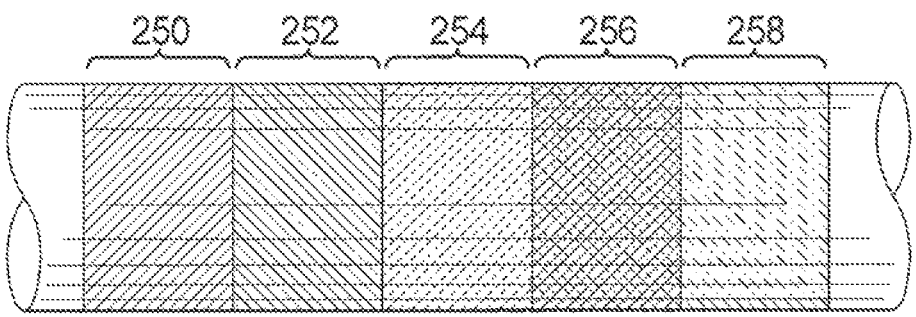
FIG. 10 is a side view of the coated medical device of FIGS. 5 to 6 including markings having different colors.

In another embodiment, a plurality of different colors are created to indicate distances from the middle point, proximal end or distal end of the medical device. The different colors are created by selectively heating a plurality of different pigments (with different properties and color shifting temperatures) above their respective color shifting temperatures. For example, in one embodiment, a progression of a plurality of uninterrupted colors is created along the length of the medical device. For illustrative purposes only, FIG. 10 illustrates one embodiment wherein a first 30 mm segment 250 of the coating of the medical wire is a first color. A second 30 mm segment 252 of the medical wire adjacent to the first segment is a second color. The adjacent segments 254, 256, and 258, each 30 mm long, are also each different colors. It should be further appreciated that a combination of one or more marking methods disclosed herein can provide a surgeon or other medical professional with additional information about the medical device. For example, the embodiment of FIG. 10 includes segments of different colors and also includes equally spaced markings of a first color, wherein the markings each indicate 10 mm of length.

Figure 11:
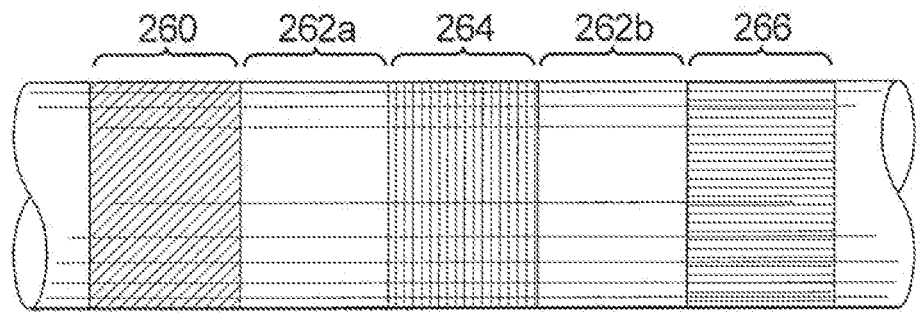
FIG. 11 is a side view of the coated medical device of FIGS. 5 to 6 including a progression of a plurality of interrupted colors along the length of the medical device.

In another embodiment, a progression of a plurality of interrupted colors is created along the length of the medical device. For illustrative purposes only, FIG. 11 illustrates one embodiment wherein a first segment 260 of the coating of the medical wire is a first color, a second segment 262a of the medical wire adjacent to the first segment has not been selectively heated and is a default, second color of the cured base material. For this example, a third segment 264 of the coating of the medical wire is a third color, a fourth segment 262b of the medical wire adjacent to the third segment has not been selectively heated and is the default, second color of the cured base material and a fifth segment 266 of the coating of the medical wire is a fourth color.

Figure 12:
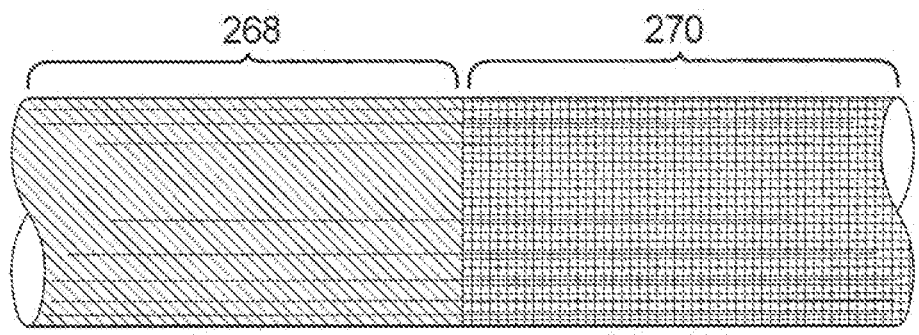
FIG. 12 is a side view of the coated medical device of FIGS. 5 to 6 including a first shifted color which runs from a distal end of the medical device to a halfway or middle point of the medical device and a second, different, contrasting color which runs from the proximal end of the medical device to the halfway or middle point of the medical device.

In another embodiment, a medical device disclosed herein includes a first shifted color (which runs from a distal end of the medical device to a halfway or middle point of the medical device) and a second, different, contrasting color (which runs from the proximal end of the medical device to the halfway or middle point of the medical device). For illustrative purposes only, FIG. 12 illustrates one embodiment wherein a first segment 268 of the medical wire (which runs from the distal end of the medical wire to a middle point) is coated and selectively heated to a first color shifting temperature to change the color of a first pigment (and thus change the color of the first segment) to a first color, such a green. As further seen in FIG. 12, a second segment 270 of the medical wire (which is of equal or substantially equal length as the first segment and runs from the proximal end of the medical wire to the middle point) is coated and selectively heated to a second color shifting temperature to change the color of a second, different pigment (and thus change the color of the second segment) to a second, different color, such as yellow. Such a configuration provides that a surgeon or medical professional can quickly identify when more than 50% of the medical device is internal to the patient and determine whether a different medical device of a different length should be employed. That is, the medical device of this embodiment (and other disclosed embodiments wherein different segments of a medical device are marked with different colors) is utilized by a surgeon or medical professional during a medical procedure to determine the length of the medical device inserted into a patient's body (i.e., by observing the color of the segments of the medical device that are external to the patient's body).

Figure 13:
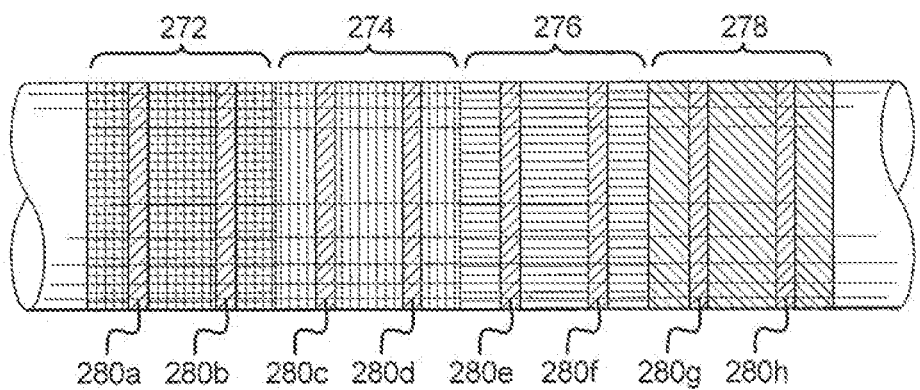
FIG. 13 is a side view of the coated medical device of FIGS. 5 to 6 including a plurality of pigments having different color shifting characteristics, wherein certain portions of the coating include a plurality of pigments that shift color.

In another embodiment, a plurality of pigments having different color shifting characteristics are included in the coating, wherein certain portions of the coating include a plurality of pigments that shift color. For illustrative purposes only, FIG. 13 illustrates one embodiment wherein a first segment 272 of the medical wire (which accounts for 25% of the length of the medical wire) is coated and selectively heated to a first color shifting temperature to change the color of a first pigment (and thus change the color of the first segment) to a first color, such as yellow. As further seen in FIG. 13, a second segment 274 of the medical wire (which accounts for another 25% of the length of the medical wire) is coated and selectively heated to a second color shifting temperature to change the color of a second pigment (and thus change the color of the second segment) to a second color, a third segment 276 of the medical wire (which accounts for another 25% of the length of the medical wire) is coated and selectively heated to a third color shifting temperature to change the color of a third pigment (and thus change the color of the third segment) to a third color and a fourth segment 278 of the medical wire (which accounts for another 25% of the length of the medical wire) is coated and selectively heated to a fourth color shifting temperature to change the color of a fourth pigment (and thus change the color of the fourth segment) to a fourth color. In this example, in addition to using heat activated pigments to shift the colors of the four segments, additional markings 280a to 280h are created along the length of the medical wire by utilizing laser activated pigments to selectively change certain portions of the medical wire a fifth color. That is, although one or more pigments located in the coating of the first segment of the medical wire were previously heat activated to change the first segment to a yellow color, additional pigments located in the coating of the first segment are laser activated to indicated marks 280a and 280b as a brown color in the first segment. Such a configuration provides that a surgeon or medical professional could utilize not only the color of the different segments of the medical device (i.e., to determine the length of the medical device inserted into a patient's body by observing the color of the segments of the medical device that are external to the patient's body) but could also count the number of marks for a segment that is partially internal and partial external to the patient's body to determine the exact length of the medical device utilized.

In another such embodiment which utilizes a plurality of pigments having different color shifting characteristics in the coating (not shown), a first segment of a coated medical device (which runs from the distal end of the medical wire to a middle point of the medical device) is selectively heated to a first color shifting temperature to change the color of a first pigment (and thus change the color of the first segment) to a first color, such a black. In this embodiment, a second segment of the medical device (which runs from the proximal end of the medical wire to the middle point) is then selectively heated to a second color shifting temperature to change the color of a second, different pigment (and thus change the color of the second segment) to a second, different color, such as yellow. In this embodiment, a third pigment located in certain portions of the first segment of the medical device are excited or otherwise activated to change to a third color, such as white (and thus create suitable markings in the first segment of the medical device) and a fourth pigment located in certain portions of the second segment of the medical device are excited or otherwise activated to change to a fourth color, such as brown (and thus create suitable markings in the second segment of the medical device).

It should be appreciated that the markings disclosed herein are not limited to indicating lengths, but also can indicate the size, type, material, part number, serial number, lot number, manufacturing date, manufacturer of the coated medical wire or medical device. The markings can also include bar codes or other codes, or other properties or instructions associated with the coated medical wire or medical device. In another embodiment, the markings disclosed herein form a band or stripe along the entire length or along selected lengths from the distal end to the proximal end of the medical device. In different embodiments, these markings can form one or more: linear lines, bands or stripes along the longitudinal axis of the medical device, spiral patterned lines, bands or stripes along the length of the medical device, parallel lines, bands or stripes, perpendicular lines, bands or stripes, transverse lines, bands or stripes, any indicia or marking disclosed herein or any combination thereof. It should be appreciated that such formed markings can be utilized in combination with any suitable marking disclosed herein to denote one or more dimensions or sizes along the length of the medical device.

In another embodiment, different heat activated pigments are utilized to denote different lengths and/or sizes of different medical devices. For example, a first medical device of a first length is heated at or above a first color shifting temperature to cause a first pigment (in the base layer applied to the first medical device) to change to a first designated color. In this example, a second medical device of a second, different length is heated at or above a second color shifting temperature to cause a second pigment (in the base layer applied to the second medical device) to change to a second designated color. Accordingly, by utilizing different heat activated pigments, different medical devices of different lengths can be properly identified without increasing or decreasing the diameter of the medical device, or significantly adversely affecting the function of the low-friction coating applied to such medical devices.

In one embodiment, a plurality of anti-microbial particles such as silver, ceramic, silver ceramic, silver oxide, glass silver or silver compounds or any suitable anti-microbial agent are applied to one or more of the surfaces of the coated medical wire to reduce and kill bacteria and other potential germs that are located on the surface(s) of the coated medical wire or otherwise incorporated into the coating formulation. In one embodiment, the anti-microbial particles are interspersed with the uncured coating. During the curing process, some of the anti-microbial particles migrate or rise to the surface of the coating in addition to the low-friction material. The anti-microbial particles are capable of killing bacteria and other harmful organisms which contact the surface of the coated medical wire while in storage or while the medical device is deployed into the body. The coated medical wire therefore minimizes or reduces the chance of infections or other complications in the body after the surgical procedure is complete.

In another embodiment, one or more of the pigments in the coating are formulated to change or shift colors a plurality of times. For example, a designated pigment in the coating is initially a green or blue color that will change or shift to a white or white/grey color with one level of laser energy. In this example, the designated pigment will further change or shift to a dark black color with another, higher or different laser energy. In one such embodiment, different types of laser energy, such as a $CO_2$ laser or a YAG laser, are utilized to create either dark or light color marks on the same coating. Accordingly, such pigments are formulated, depending on the different levels of applied laser energy, different laser types or different color shifting temperatures, to provide a plurality of different color markings on a single medical device.

In another embodiment, a radiopaque material, such as barium sulfide, barium sulfate or a suitable metal, such as tungsten, is added to the coating. In this embodiment, a suitable marking is provided or shows up using a suitable imaging device, such as an x-ray device, a magnetic resonance imaging (MRI) device, or an ultrasound device. In one such embodiment, the imaging device displays an image of the radiopaque marking on one or more display devices of the imaging device. In another such embodiment, the imaging device produces an image of the radiopaque marking on a film or other suitable media, such as by producing an x-ray film. In these embodiments, the surgeon or other medical professional utilize the imaging device to determine an exact location of the medical device inside a patient and/or to determine one or more measurements inside the patient.

Figure 14:
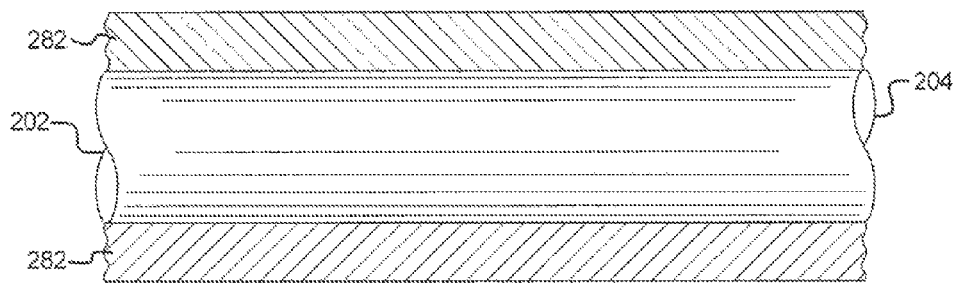
FIG. 14 is a side view, partially in section, of the medical device of FIG. 2 including a low-friction coating applied to the surface thereof.

In another embodiment, a base layer including a low-friction material, such as PTFE, is applied to a surface of the medical device. The medical device and the applied base layer are then heated above a first designated temperature to cure the coating. For example, as seen in FIG. 14, a base layer of a low-friction material 282 is applied to the outer surface of the medical device.

Figure 15:
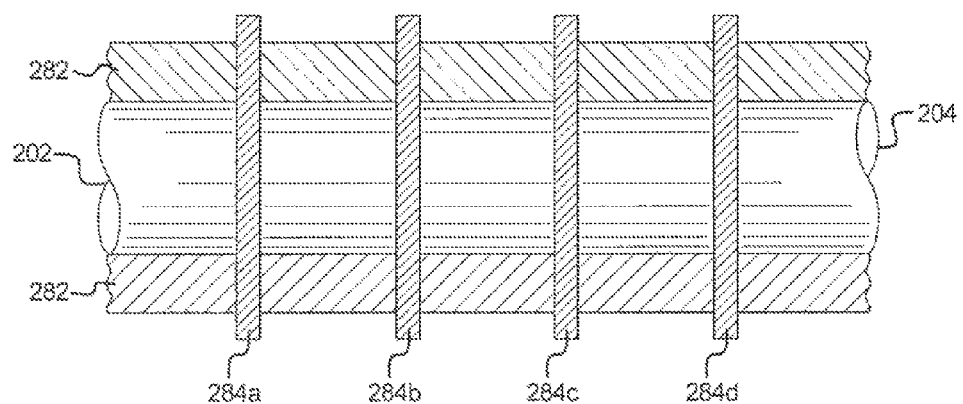
FIG. 15 is a side view, partially in section, of the medical device of FIG. 14 after a plurality of bands of a radiopaque material are applied to the low-friction coating of the medical device.

After curing the medical device and the applied base layer, a radiopaque material is selectively bonded to spaced apart portions of the surface of the coated medical device. The coated medical device and the applied radiopaque material are then heated above a second designated temperature to cure the radiopaque material. For example, as seen in FIG. 15, the radiopaque material is bonded to different, spaced apart areas of the medical device to form discrete bands 284a, 284b, 284c and 284d of the radiopaque material. In this example embodiment, a suitable amount or density of the radiopaque material is selectively bonded to the surface of the coated medical device such that the radiopaque material is detectable when the medical device is viewed using a suitable imaging device. Thus, the medical device of this embodiment includes a plurality of discrete markings of a radiopaque material protruding from or situated above a low-friction coating. Accordingly, the resulting medical device will have different slightly elevated bands or areas along the length of the medical device (such as to indicate distance), have low-friction characteristics (including low friction, low surface energy and/or non-stick characteristics) and include markings that show up using a suitable imaging device to provide an exact location of the medical device inside a patient for safety and/or measurement purposes.

In one embodiment, a clear or slightly pigmented low-friction top-coating is applied to the radiopaque coated medical device. For example, the clear or slightly pigmented applied low-friction top coat includes one or more suitable fluoropolymers or low-friction particles, one or more particles of a hydrophilic material and a binder, such as polyarylsulfone. In this embodiment, the clear or slightly pigmented low-friction top coat accounts for the valleys created between the slightly elevated radiopaque bands to provide that the medical device includes a substantially smooth surface. For example, a clear or slightly pigmented low-friction top coated is applied to the radiopaque coated medical device and the applied top coating is then suitably or partially cured. In this example, the medical device is then passed thru a round die which removes any excess partially cured topcoat and leaves the topcoat in the depressions caused by the slightly elevated bands of radiopaque material as described above. In this example, the remaining topcoat is then fully cured to provide a medical device with a substantially smooth, low-friction surface.

Figure 16:
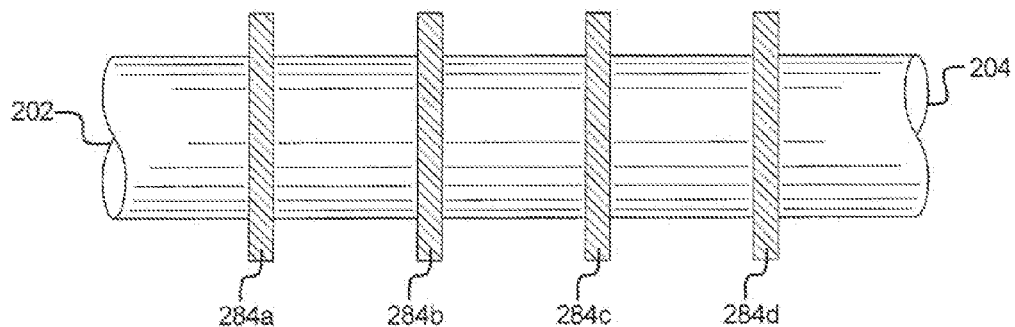
FIG. 16 is a side view, partially in section, of the medical device of FIG. 2 including a plurality of bands of a radiopaque material applied to the surface thereof.

In another embodiment, a radiopaque material is selectively bonded to spaced apart portions of a surface of the otherwise uncoated medical device. In this embodiment, a suitable amount or density of the radiopaque material is selectively bonded to the surface of the medical device such that the radiopaque material is detectable when the medical device is viewed using a suitable imaging device. For example, as seen in FIG. 16, a radiopaque material is bonded to different spaced apart areas of the medical device to form discrete bands 284a, 284b, 284c and 284d of the radiopaque material.

Figure 17:
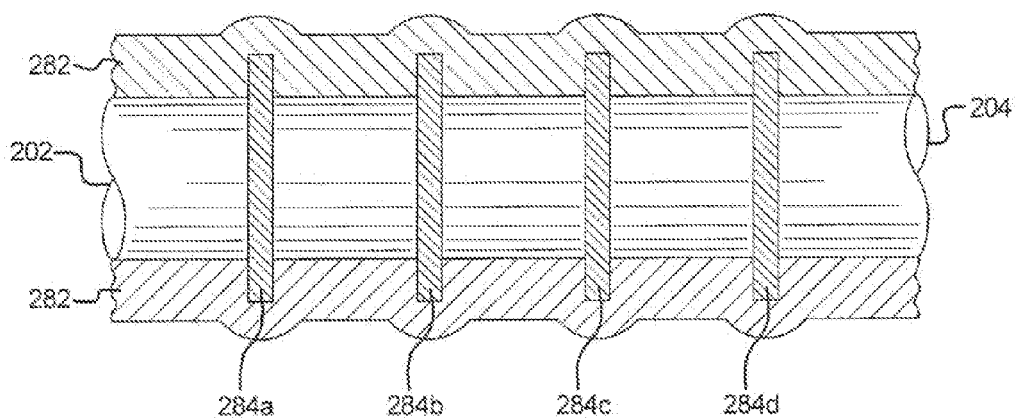
FIG. 17 is a side view, partially in section, of the medical device of FIG. 16 after a low-friction top coat is applied to bands of the radiopaque material and the uncoated portions of the medical device.

After selectively bonding the radiopaque material to a surface of the medical device, the medical device (which includes the radiopaque material) is heated above a first designated temperature to cure the radiopaque material. After curing the medical device, a low-friction material, such as PTFE or other low-friction material, is applied to the surfaces of the medical device (including over the selectively bonded areas of radiopaque material). The coated medical device and the low-friction material are then heated above a second designated temperature to cure the coating of the low-friction material. For example, as seen in FIG. 17, a low-friction material 282 is applied to an outer surface of the bonded radiopaque material and the remaining uncoated outer surfaces of the medical device. It should be appreciated that by first selectively applying the radiopaque material to a surface of the medical device and then applying the low-friction coating, the radiopaque material is covered with the low-friction material to provide that the entire surface of the medical device exhibits low-friction properties. Accordingly, the resulting medical device will have different elevated areas or bands along the length of the medical device (such as to indicate distance), have low-friction characteristics (including low friction, low surface energy and/or non-stick characteristics) and include markings that show up using a suitable imaging device to provide an exact location of the medical device inside a patient for safety and/or measurement purposes.

Figure 18:
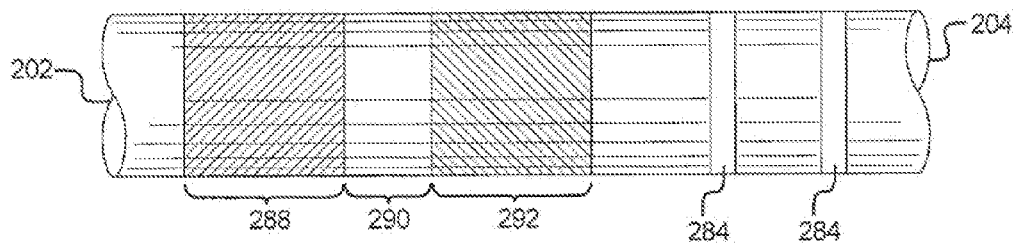
FIG. 18 is a side view of a medical device of FIG. 2 including a first portion of the medical device which illustrates a plurality of markings resulting from shifting the color of selected areas of a base layer of a coating and a second portion of the medical device which illustrates a plurality of bands of radiopaque material and a low-friction coating.

In another embodiment, certain areas of the medical device are marked using color shifting pigments (as described above) and radiopaque materials are applied to certain other spaced apart areas of the medical device. In one such embodiment, a suitable radiopaque material is applied to a first portion of a medical wire that is inserted into a patient and a second portion of the medical wire that is not inserted into the patient is marked using the above-described color shifting pigments. For example, as seen in FIG. 18, a first segment 286 of the medical device includes a first area 288 which has been selected heated and is a first color, a second area 290 which has not been selectively heated and is a default second color and a third area 292 which has been selected heated and is a third color. In this example, the medical device includes a second area 294 with discrete bands of a radiopaque material 282 and a low-friction material 284 applied to an outer surface of the radiopaque material and the remaining uncoated outer surfaces of the medical device. It should be appreciated that in this embodiment, a surgeon or other medical professional can utilize (1) the portion of the medical wire that is inserted into the patient and a suitable imaging device, and (2) the visibly marked portion of the medical wire not inserted inside the patient to determine the length of the medical wire inserted into a patient's body, the length of certain elements into a patient, and the exact location of certain elements inside a patient.

In different embodiments, the radiopaque material is applied to the medical device to form one or more patterns. Such patterns include, but are not limited to: one or more horizontal lines, bands or stripes, one or more substantially horizontal lines, bands or stripes, one or more longitudinal spiral shaped lines, bands or stripes. In such embodiments, the longitudinal spiral shaped markings enable a medical professional to determine if the spiral shaped markings move and thus determine: (i) if the medical device is making progress advancing in the patient and (ii) if the medical device is rotating (in place) in the patient. It should be appreciated that the radiopaque material may be applied to the medical device to create any suitable indicia or markings, such as one or more: bands which indicate distance (as described above), parallel lines, bands or stripes, perpendicular lines, bands or stripes, transverse lines, bands or stripes, axial lines, bands or stripes, longitudinal lines, bands or stripes, spiral patterned lines, bands or stripes, numbers, bar codes, and/or marks which indicate the size, type, material, part number, serial number, lot number, manufacturing date, instructions for use, manufacturer of the medical device, any indicia or marking disclosed herein or any combination thereof.

In another embodiment, a plurality of anti-microbial particles such as silver, ceramic, silver ceramic, silver oxide, glass silver or silver compounds or any suitable anti-microbial agent are included in the low-friction coating and/or otherwise applied to one or more of the surfaces of the coated medical device. In this embodiment, the anti-microbial particles reduce and kill bacteria and other potential germs or pathogens that are located on the surface(s) or come in contact with the surface(s) of the coated medical device or otherwise incorporated into the coating formulation. Accordingly, such a medical device includes anti-microbial properties and one or more bands of radiopaque material that may be viewed with a suitable imaging device.

In another embodiment, a clear or transparent top coat is applied to one or more of the surfaces of the coated medical device after the visible marks are created in the base coating. In one embodiment, the top coating is a low-friction or release coating or material, such as fluorinated materials, polytetrafluoroethylene, perfluoro-alkoxy, fluoroethylenepropylene, MFA, polyethylene, silicone, ceramic composites, paralyene silane polymers and other suitable low-friction coatings. Such a top coating provides that the markings described above are substantially covered or sealed underneath an additional layer skin of a low friction coating. It should be appreciated that this additional layer is applied in a separate operation either after the color shift marks are created or after the marks are created in the base coat. In another embodiment, an ultraviolet cure ("uv cure") low-friction, thin layer of a special, clear, unpigmented, uv cure resin/fluoropolymer or resin/polyethylene material is formed over the marked medical device after the base coating is applied, cured and post marked. This lowers the friction of the surface since no heat is used to cure the uv material and no change in the marked lower base coating takes place which may be employed for lower temperature base materials like plastics or high friction reinforced plastics.

In another embodiment, a steel medical wire is treated with an iron, zinc, or manganese phosphate, which penetrates the steel surface and coats the surface of the medical wire with a thin layer of the phosphate, which promotes the adhesion of a coating, improves corrosion resistance, and improves the chemical protection of the medical wire. In another embodiment, conversion coating or anodizing of an aluminum medical wire is employed to promote adhesion of a coating to the medical wire and increase the surface hardness and corrosion resistance of the medical wire.

In another embodiment, at designated points on the medical device, the color shifting material is applied and the marks are created in a gradation of successively, incrementally darker colors by using gradually increasing or higher energy levels in directly adjacent areas to create a progressively darker and darker mark to further enhance the ability of the device manufacturer to create distance codes or even directional force guides on the medical device. This gradation of color shift method can be combined with cessation of energy input to create "breaks" in the color gradation to denote distance marks which are of the original color and are notably different from the gradation of darker markings.

Figure 19:
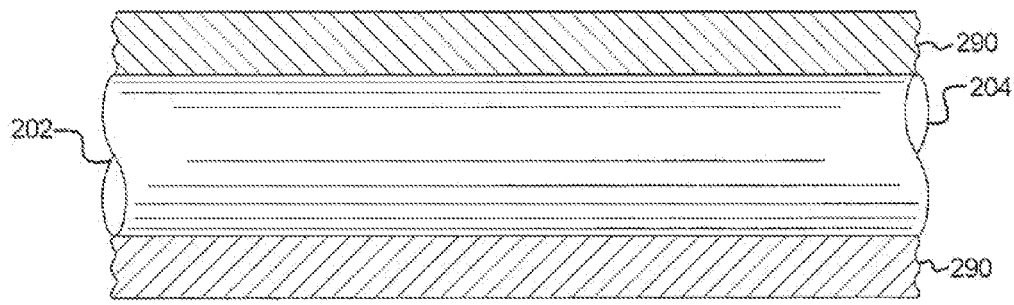
FIG. 19 is a side view, partially in section, of the medical device of FIG. 2 including a first low-friction coating applied to the surface thereof.

In another embodiment, as seen in FIG. 19, a first or base low-friction coating 290 including a low-friction material, such as PTFE, is applied to a surface of the medical device and suitably cured (or slightly undercured) to 300° F. (148.9° C.). For example, a layer approximately fifteen (15) microns thick of the first low-friction coating is applied to a surface of the medical device. In different embodiments, the first coating is a Xylan® 1514 low-friction coating with the appropriate pigments, a VICOTE™ 700 Series coating with the appropriate pigments, a VICOTE™ 800 Series coating with the appropriate pigments, a DuPont™ 420 Series coating with the appropriate pigments, a DuPont™ 257N504 coating with the appropriate pigments, a DuPont™ 851N504 coating with the appropriate pigments, a WHITFORD OC 600 Series coating with the appropriate pigments, a WHITFORD OC 8800 Series coating with the appropriate pigments, an MPC 992003 coating with the appropriate pigments, a Ultralon® OC Series coating with the appropriate pigments, a Fluoroplate® 41141 Series coating with the appropriate pigments manufactured by Orion Industries, or any suitable coating. In one such embodiment, the first low-friction layer includes a first relatively light colored pigment, such as titanium dioxide (i.e., a white colored pigment). In one such embodiment, a radiopaque pigment, such as barium sulfate is utilized in the first or base low-friction coating. In this embodiment, the radiopaque pigment provides both a visually white or near white colored PTFE coating and a slight radiopaque visibility when used in a fluoroscope environment. In another embodiment, the first or base low-friction coating includes one or more metal oxide pigments, and/or one or more Food and Drug Administration ("FDA") non-objection status for food contact approved end use pigments.

Figure 20:
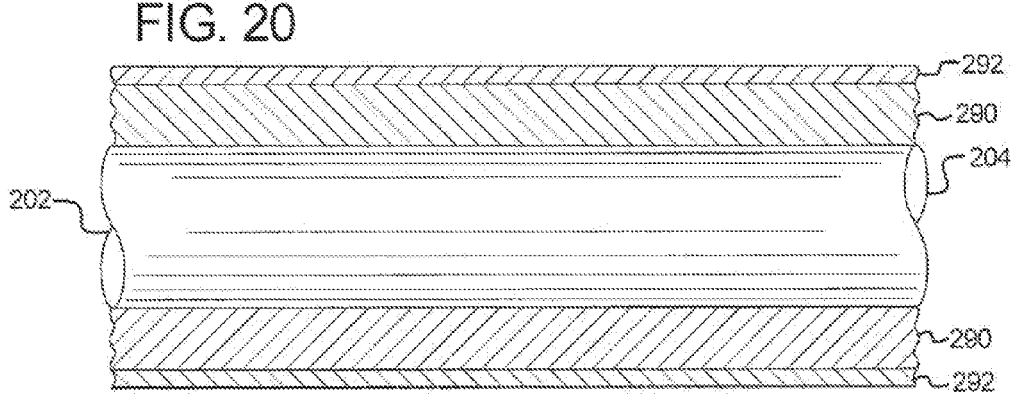
FIG. 20 is a side view, partially in section, of the medical device of FIG. 19 after a second low-friction coating is applied to the coated surface of the medical device.

As seen in FIG. 20, after applying the first low-friction layer, a second low-friction coating 292, including a low-friction material, such as PTFE, is applied to the coated surface of the medical device and suitably cured to at least 700° F. (371.1° C.) to fuse the two coatings together. For example, a layer approximately five (5) microns thick of the second low-friction coating is applied to the previously coated surface of the medical device. In one embodiment, the second low-friction coating includes one or more pigments which contrast in color and/or hue to one or more pigments in the first low-friction coating. In one such embodiment, the second low-friction layer includes a second relatively dark colored or hued pigment, such as a green, black or blue colored pigment (which contrasts in color and/or hue to a first relatively light colored pigments in the first low-friction coating). In different embodiments, the second coating is a Xylan® 1514 low-friction coating with the appropriate pigments, a VICOTE™ 700 Series coating with the appropriate pigments, a VICOTE™ 800 Series coating with the appropriate pigments, a DuPont™ 420 Series coating with the appropriate pigments, a DuPont™ 257N504 coating with the appropriate pigments, a DuPont™ 851N504 coating with the appropriate pigments, a WHITFORD OC 600 Series coating with the appropriate pigments, a WHITFORD OC 8800 Series coating with the appropriate pigments, an MPC 992003 coating with the appropriate pigments, a Ultralon® OC Series coating with the appropriate pigments, a Fluoroplate® 41141 Series coating with the appropriate pigments manufactured by Orion Industries, or any suitable coating with pigments and a laser sensitive pigment to assist in ablation. In one embodiment, the second low-friction coating includes one or more metal oxides pigments and/or one or more ceramic, or FDA approved non-objection status for food contact end use pigments.

It should be appreciated that in different embodiments, the different coatings used for the first and second low-friction coatings depend, at least in part, on the types of sterilization methods used to sterilize the coated medical device disclosed herein. In one such embodiment, the first and/or second low-friction coatings are fully capable of being sterilized using gamma radiation.

In this embodiment, after applying the two low-friction layers of contrasting colored coating, an amount of energy is selectively applied to different spaced apart areas of the coated medical device. For example, a CO2 laser of 0.25 watts to 5.0 watts is selectively applied to different, spaced apart areas of the coated medical device. In another example, a YAG laser using 10 watts of power, with 3000 speed and 500 frequency is used separately or sequentially on the coated medical device to provide different ablations of the second low-friction layer. It should be appreciated that the laser ablates or removes the second or outer low-friction layer while not significantly affecting the first low-friction layer. That is, the second low-friction layer with the relatively dark colored pigment absorbs the applied energy (or part of the absorbed energy) and is accordingly vaporized or ablated from the medical device, while the first low-friction layer with a relatively light colored pigment does not absorb the applied energy (or absorbs less of the applied energy) and is thus not affected by the applied energy. Thus, even after one low-friction layer has been removed, the medical device retains at least another low-friction layer to provide low friction properties along the length of the medical device.

Figure 21:
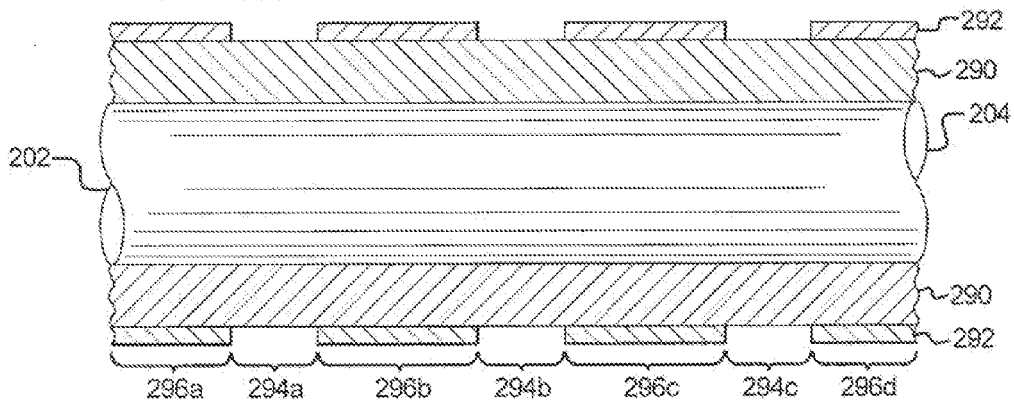
FIG. 21 is a side view, partially in section, of the coated medical device of FIG. 20 after areas of the second low-friction coating have been removed.

As seen in FIG. 21, after the amount of energy, such as the laser is selectively applied to different spaced apart areas of the medical device, the outer surfaces of the laser applied areas of the medical device 294a, 294b and 294c will include the first low-friction, light colored coating and the outer surfaces of the non-laser applied areas of the medical device 296a, 296b, 296c and 296d will include the second low-friction dark colored coating. It should be appreciated that since a thin layer of the dark colored low-friction material is applied to the medical device, when that thin layer is removed from the medical device, any grooves or valleys in the surface of the low-friction coating will be relatively shallow and not create any substantially sharp edged shoulders which can scrape bodily tissues, snag vessels or arteries of the patient, or otherwise cause damage and/or trauma to the patient. Accordingly, in this embodiment, the medical device includes at least one suitable low-friction coating applied to the outer surface of the medical device, wherein different areas of the medical device are suitably marked with different colors. As described above, such different colored areas along the surface of the low-friction coated medical device indicate to surgeons or other medical professionals the length of the medical device that is inserted into a patient.

Figure 22:
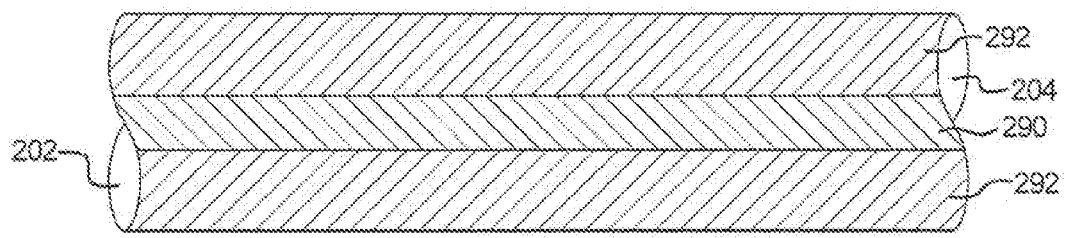
FIG. 22 is a side view of a coated medical device of FIG. 21 including a first area with the applied second low-friction coating and a second, horizontal line shaped area with the second low-friction coating removed.

In another embodiment, a band or stripe is created along the entire or selected lengths from the distal end to the proximal end of the medical device. In one such embodiment, this stripe or band can be linear along the longitudinal axis of the medical device. For example, as seen in FIG. 22, portions of the second low-friction coating 292 are removed from the medical device to form a first designated pattern of the first low-friction coating 290, such as a horizontal line that is 2 mm wide. In another example (not shown), a plurality of portions of the second low-friction coating, such as two portions spaced 180 degrees apart from each other, are removed from the medical device to form a plurality of horizontal lines. In different embodiments, a laser is moved along the length of the medical device, the medical device is moved relative to the laser or any combination thereof to create such a horizontal or substantially horizontal line.

Figure 23:
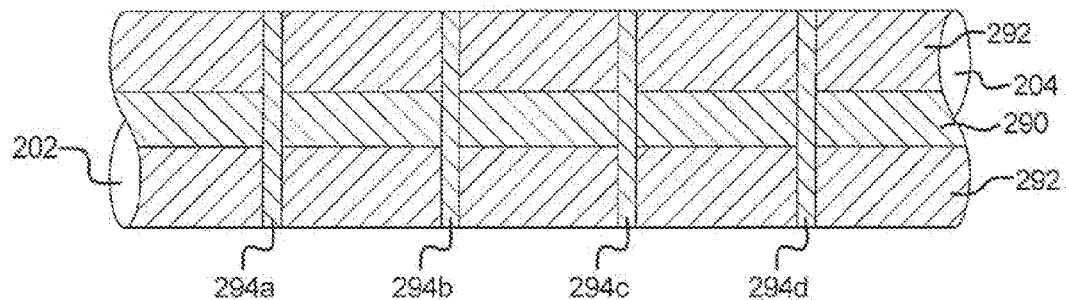
FIG. 23 is a side view of the coated medical device of FIG. 22 including a plurality of areas of the second low-friction coating removed to form a plurality of markings along the length of the medical device.

In another embodiment, the created horizontal stripe marking(s) are utilized in combination with circumferential bands of one or more specified dimensions or sizes (as described above) along the length of the medical device to indicate distance. In this embodiment, the combination of different markings provide surgeons or other medical professionals suitable information regarding: (i) the length of the medical device that is inserted into a patient, (ii) if the medical device is moving in the patient (as required by the medical professional), and/or (iii) if the medical device is rotating in the patient (as required by the medical professional). In one such embodiment, the second low-friction coating is selectively ablated to form a linear stripe or band and one or more markings to indicate distance. For example, as seen in FIG. 23, after the second low-friction coating has been selectively removed, the coated medical device includes a first designated pattern of the first low-friction coating 290 and a plurality of markings of the first low-friction coating 294a to 294d along the length of the medical device.

Figure 24:
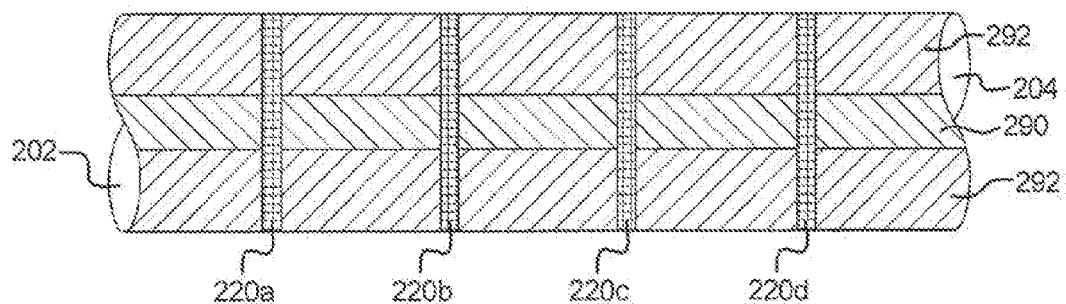
FIG. 24 is a side view of the coated medical device of FIG. 22 including a plurality of markings along the length of the medical device which result from applying energy to energy sensitive particles in the coating to shift the color of selected areas of the coating.

In another such embodiment, the first and/or second low-friction coatings include a plurality of heat sensitive pigments as described herein. In this embodiment, the second low-friction coating is selectively ablated to form a linear stripe or band and a plurality of portions of the coated medical device are selectively heated (to shift the color of such heat sensitive pigments) to create a plurality of markings to indicate distance. For example, as seen in FIG. 24, the second low-friction coating is selectively removed to create a first designated pattern of the first low-friction coating 290 and a plurality of markings 220a to 220d are created along the length of the medical device by selective heating portions of the coating above a color shifting temperature while simultaneously maintaining adjacent portions of coating at a cooler temperature.

Figure 25:
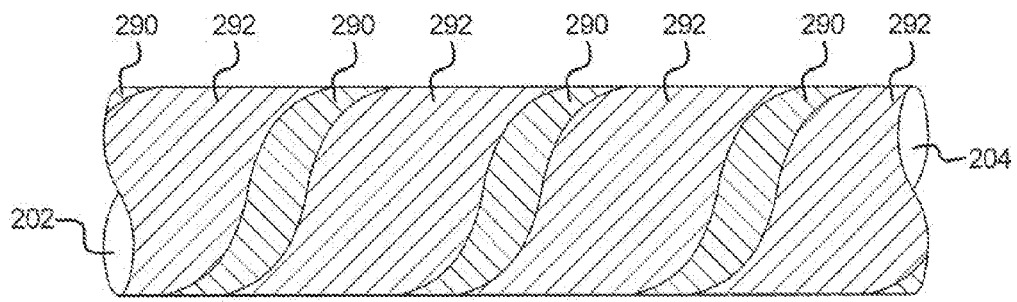
FIG. 25 is a side view of a coated medical device of FIG. 21 including a first area with the applied second low-friction coating and a second, spiral shaped area with the second low-friction coating removed.

In another such embodiment, the created stripe or band can be a spiral shaped pattern along the length of the medical device. For example, as seen in FIG. 25, portions of the second low-friction coating 292 are removed from the medical device to form a second designated pattern of the first low-friction coating 290, such as a 2 mm wide longitudinal spiral marking that continues in a spiral pattern for the length of the medical device. In different embodiments, the medical device is rotated while the laser is moved along the length of the medical device, the medical device is rotated and simultaneously moved relative to the laser or any combination thereof. In such embodiments, the longitudinal spiral markings enable a medical professional to determine if the inserted medical device is rotating in place and also to determine if the spiral markings move to determine if the medical device is making progress or otherwise advancing in the patient.

Figure 26:
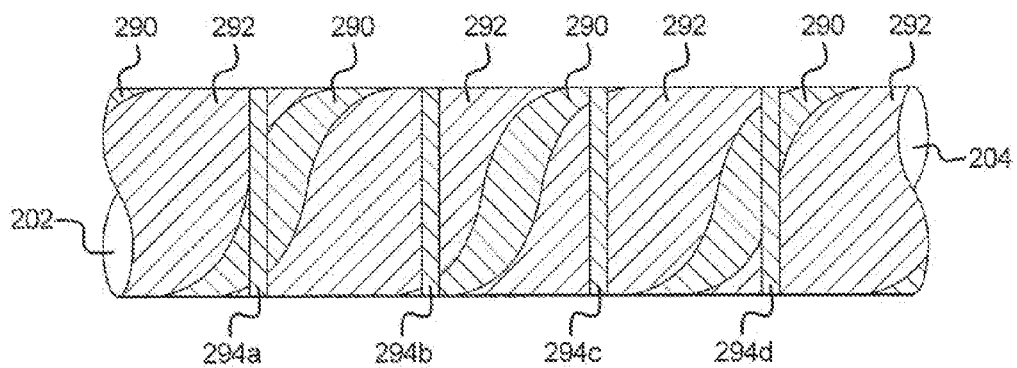
FIG. 26 is a side view of the coated medical device of FIG. 25 including a plurality of areas of the second low-friction coating removed to form a plurality of markings along the length of the medical device.

In another embodiment, the created longitudinal spiral shaped markings are utilized in combination with circumferential bands of one or more specified dimensions or sizes (as described above) along the length of the medical device to indicate distance. In this embodiment, the combination of different markings provide surgeons or other medical professionals suitable information regarding: (i) the length of the medical device that is inserted into a patient, (ii) if the medical device is moving in the patient (as required by the medical professional), and/or (iii) if the medical device is rotating in the patient (as required by the medical professional). In one such embodiment, the second low-friction coating is selectively ablated to form a longitudinal spiral stripe or band and one or more markings to indicate distance. For example, as seen in FIG. 26, after the second low-friction coating has been selectively removed, the coated medical device includes a first longitudinal spiral pattern of the first low-friction coating 290 and a plurality of markings of the first low-friction coating 294a to 294d along the length of the medical device.

Figure 27:
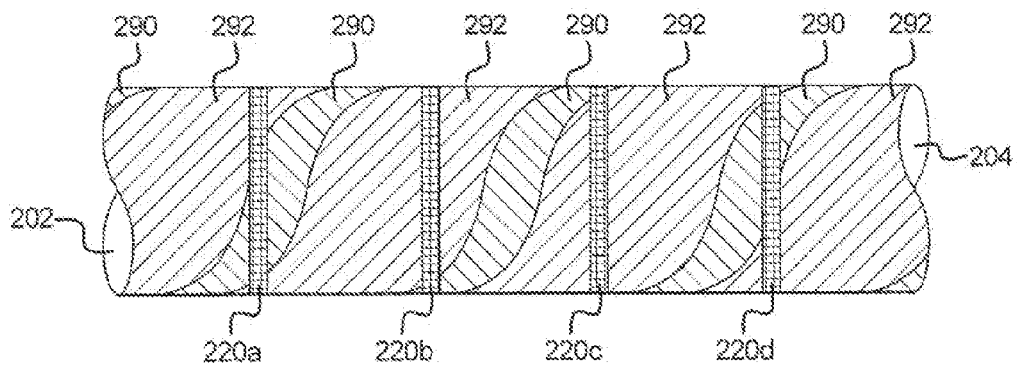
FIG. 27 is a side view of the coated medical device of FIG. 25 including a plurality of markings along the length of the medical device which result from applying energy to energy sensitive particles in the coating to shift the color of selected areas of the coating.

In another such embodiment, the first and/or second low-friction coatings include a plurality of heat sensitive pigments as described herein. In this embodiment, the second low-friction coating is selectively ablated to form a longitudinal spiral stripe or band and a plurality of portions of the coated medical device are selectively heated (to shift the color of such heat sensitive pigments) to create a plurality of markings to indicate distance. For example, as seen in FIG. 27, the second low-friction coating is selectively removed to create a designated longitudinal spiral pattern of the first low-friction coating 290 and a plurality of markings 220a to 220d are created along the length of the medical device by selective heating portions of the coating above a color shifting temperature while simultaneously maintaining adjacent portions of coating at a cooler temperature.

It should be appreciated that in different embodiments, the outer low-friction coating may be removed from the medical device to create contrasting colors that provide any suitable indicia or markings, such as one or more: bands, parallel lines, bands or stripes, perpendicular lines, bands or stripes, transverse lines, bands or stripes, axial lines, bands or stripes, longitudinal lines, bands or stripes, spiral patterned lines, bands or stripes, numbers, bar codes, and/or marks which indicate the size, type, material, part number, serial number, lot number, manufacturing date, instructions for use, manufacturer of the medical device, any indicia or marking disclosed herein or any combination thereof.

In another embodiment, a clear or slightly pigmented low-friction top-coat, such as PFTE, particles of one or more suitable fluoropolymers or particles of a hydrophilic material, is applied to the laser ablated medical device. In this embodiment, the clear or slightly pigmented low-friction top coat accounts for the removed ablated areas of the medical device to provide a substantially smooth surface. That is, the low-friction top coat fills in the relatively shallow valleys which are created by laser ablating the second low-friction coating to create a medical device with different colored portions and a substantially continuous substantially smooth surface. For example, 5 microns of a clear or slightly pigmented low-friction top coat is applied to the laser ablated medical device and the applied coating is then suitably or partially cured. In one such embodiment, the medical device is then passed thru a round die which removes any excess partially cured topcoat and leaves the topcoat in the depressions that are caused by the laser ablation as described above. The remaining topcoat is then fully cured to provide a medical device with different contrasting colors and a substantially smooth, low-friction surface.

It should be appreciated that any suitable color or color combination may be utilized in association with the low-friction coated medical device. In different embodiments, the available color choices of the different low-friction coatings are all the prime colors, any suitable combination of the prime colors, any color or color combination from the red, blue and yellow spectrums as well as any suitable black, white or gray color. For example, the color combinations include a white or other light color first low-friction or base coating and a green or blue contrasting color second low-friction coating.

In another embodiment, the medical device disclosed herein includes a relatively dark colored first or base low-friction layer and a relatively light colored second low-friction layer. In one such embodiment, the relatively dark first low-friction layer is suitably treated to withstand the laser energy. In different embodiments, the relatively dark first low-friction layer is treated by using a suitable "alloy" material, such as aluminum or by using a suitable "leafing" material, such as mica. In this embodiment, such additions to the first low-friction layer protects the first low-friction layer from the laser energy.

In another embodiment, a plurality of contrasting colored low-friction coatings are applied to a surface of the medical device. In this embodiment, along one or more designated portions of the medical device, the outer coating is removed or ablated using a pattern of micro-dots, micro-marks or micro-ablations. Such ablation utilizing micro-dots or micro-marks provides that the ablated portion of the medical device appears, without magnification, as the contrasting color or hue of the inner low-friction coating. It should be appreciated that utilizing such micro-dots, micro-marks or micro-ablations to ablate or remove the outer low-friction coating further provides a tactile smooth outer layer even though micro-dot portions of the outer low-friction coating is removed. That is, the outer low-friction coating feels unbroken to the medical professional (i.e., due to the "pillars" of the outer coating which remain) even though there is a color contrast between the micro-dot ablated portions of the medical device and the non-micro-dot ablated portions of the medical device.

In another embodiment, one or more color shifting pigments (as described herein) are included in the first low-friction coating and/or the second low-friction coating. In this embodiment, in addition to ablating the second low-friction coating (along certain portions of the medical device) to expose the contrasting color of the first low-friction coating, one or more portions of the medical device are selectively heated above a color shifting temperature to change the color of such color shifting pigments. This embodiment thus provides a marked medical device with a plurality of different colored sections.

In another embodiment, in addition to ablating the second low-friction coating (along certain portions of the medical device) to expose the contrasting color of the first low-friction coating, other portions of the second low-friction coating are overheated with external heat to create another color on the marked medical device. For example, a medical device will have alternating green and white markings as a result of the laser removal of the second or outer low-friction coating as described above. In this example, a subsequent heat process using a non-laser energy source, such as infrared heat, hot air or direct contact with a heat source, will change the color of different areas of the second low-friction coating to a darker color while not substantially altering the low friction properties of this second low-friction coating. Such a resulting medical device includes a clearly visible green color with alternating white color markings around the medical device and one or more black or dark colored bands at specific areas along the medical device. Accordingly, this example coated medical device will include a first white colored portion (i.e., the portion where the first low-friction coating is exposed), a second green colored portion (i.e., the portion where the second low-friction coating is exposed) and a third black colored portion (i.e., the portion where the second low-friction coating is overheated). In one such embodiment, two types of lasers are utilized to provide a medical device with a partially ablated topcoat and a partially overheated topcoat. In another such embodiment, one or more heat sensitive pigments (as described herein) are included in the second low-friction coating to create a color shift of the second low-friction coating when the second low-friction coating is heated above a suitable color shifting temperature. In another embodiment, a clear or partially pigmented low-friction top coat is applied to this medical device to provide a smooth surface.

In another embodiment, a plurality of anti-microbial particles such as silver, ceramic, silver ceramic, silver oxide, glass silver or silver compounds or any suitable anti-microbial agent are included in the first low-friction coating, included in the second low-friction coating and/or otherwise applied to one or more of the surfaces of the coated medical device. In this embodiment, the anti-microbial particles reduce and kill bacteria and other potential germs that are located on the surface(s) of the coated medical device or otherwise incorporated into the coating formulation.

In another embodiment, a radiopaque material, such as barium sulfide, barium sulfate or a suitable metal, such as tungsten, is included in the first low-friction coating, included in the second low-friction coating and/or otherwise applied to one or more of the surfaces of the coated medical device. In this embodiment, the radiopaque material provides that a suitable marking shows up when using a suitable imaging device. In these embodiments, the surgeon or other medical professional utilize the imaging device to determine an exact location of the medical device inside a patient and/or to determine one or more measurements inside the patient.

In another embodiment, a plurality of low-friction coatings are applied to the medical device. In this embodiment, one or more of the low-friction coating are subsequently removed to denote different markings along the medical device. In one such embodiment, three different colored low-friction coatings are applied to the medical device wherein different coatings are selectively removed at different portions of the medical device to denote different information to the medical professional. For example, three different colored low-friction layers can be utilized wherein a suitable amount of laser energy removes the top two low-friction layers and retains the bottom low-friction layer to denote a mid-point of a medical device (or to denote other suitable markings). In another example, three different colored low-friction layers can be utilized wherein a suitable amount of laser energy (and/or a different type of energy) removes all three low-friction layers to leave the bare metal substrate exposed to denote a mid-point of a medical device (or to denote other suitable markings). In these example, different types of laser energy may be used, such as a $CO_2$ laser and a separate YAG laser, for the selective removal of different ones of the low-friction layers.

In another embodiment, a single low-friction coating is applied to the medical device. In this embodiment, different portions of the applied low-friction coating are removed or ablated (using laser energy or other suitable energy) to leave the bare metal substrate exposed. In different embodiments, the low-friction coating may be removed from the medical device to create contrasting colors (between the low-friction coating and the bare metal substrate) that provide any suitable indicia or markings, such as one or more: bands, parallel lines, bands or stripes, perpendicular lines, bands or stripes, transverse lines, bands or stripes, axial lines, bands or stripes, longitudinal lines, bands or stripes, spiral patterned lines, bands or stripes, numbers, bar codes, and/or marks which indicate the size, type, material, part number, serial number, lot number, manufacturing date, instructions for use, manufacturer of the medical device, any indicia or marking disclosed herein or any combination thereof.

In another embodiment, a plurality low-friction coatings are applied to the medical device. In this embodiment, for at least one portion of the medical device, the applied low-friction coatings are removed or ablated (using laser energy or other suitable energy) to leave the bare metal substrate exposed. In different embodiments, one, more or each the low-friction coatings may be removed from the medical device to create contrasting colors (between one of the low-friction coatings and the bare metal substrate or between two contrasting colored low-friction coatings) that provide any suitable indicia or markings, such as one or more: bands, parallel lines, bands or stripes, perpendicular lines, bands or stripes, transverse lines, bands or stripes, axial lines, bands or stripes, longitudinal lines, bands or stripes, spiral patterned lines, bands or stripes, numbers, bar codes, and/or marks which indicate the size, type, material, part number, serial number, lot number, manufacturing date, instructions for use, manufacturer of the medical device, any indicia or marking disclosed herein or any combination thereof.

In another embodiment, after one or more low-friction coatings have been removed, a vibratory bath with appropriate particles and fluids is utilized to slightly polish the coated outer surfaces of the medical device. In this embodiment, the vibratory bath selectively radiuses or polishes the diameter of the coated medical device to result in a smoother transition from the exposed first low-friction coating to the second low-friction coating. In one such embodiment, the particles contained within the vibratory bath are a plastic/ceramic abrasive to gently abrade the edges of the protruding bands of the coating. These particles are wetted continuously with appropriate fluids that contain various agents to assist in dispersing the dislodged low-friction particles that have been removed during the vibratory process. In one such embodiment, the processed medical device is then ultrasonically degreased in an aqueous solution to remove any remaining particles.

In different embodiments, an additional hydrophilic top coat is applied to one or more of the different coated medical devices disclosed herein. In one such embodiment, a hydrophilic top coat is applied over one or more coatings which include one or more energy sensitive pigments. In another such embodiment, a hydrophilic top coat is applied over one or more coatings which include one or more bands of radiopaque materials. In another such embodiment, a hydrophilic top coat is applied over one or more medical devices which include at least one area of an outer low-friction coating removed to reveal an inner low-friction coating of a contrasting color. In these embodiments, a hydrophilic top coat is applied to one or more areas or portions of such medical devices to provide an additional low-friction coating. In one such embodiment, the hydrophilic top coat is applied to the previously applied low-friction coating and then suitably heat or UV cured to adhere the hydrophilic top coat to the low-friction coating.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of manufacturing a coated medical device, said method comprising:
   (a) applying a coating to at least two different portions of a metal outer surface of a medical device, said coating including:
      (i) a binder,
      (ii) a plurality of particles of a low-friction material, and
      (iii) a pigment;
   (b) for at least a first one of the portions of the metal outer surface of the medical device:
      (i) partially curing said coating, said curing causing said plurality of particles to form a low-friction top coat;
      (ii) applying a plurality of radiopaque particles to the low-friction top coat; and
      (iii) further curing said coating; and
   (c) for at least a second, different one of the portions of the metal outer surface of the medical device:
      (i) curing said applied coating to cause the low-friction particles to migrate from first positions below the pigment in the coating to second positions above the pigment in the coating, and
      (ii) heating the cured coating such that the pigment of the cured coating is heated above a color shifting temperature to cause said pigment to change from a first color to a second different color without substantially degrading the low-friction material of the cured coating.

2. The method of claim 1, wherein applying the plurality of radiopaque particles includes applying the plurality of radiopaque particles to a plurality of spaced-apart portions of the low-friction top coat.

3. The method of claim 1, which includes selectively heating a designated quantity of portions of the cured coating such that the pigment of each selectively heated portion of the cured coating is heated above a color shifting temperature to cause said pigment to change from a first color to a second different color without substantially degrading the low-friction material of each selectively heated portion of the cured coating.

4. The method of claim 1, wherein for the at least the first one of the portions of the metal outer surface of the medical device, partially curing said coating includes causing the low-friction particles to migrate from first positions below the pigment in the coating to second positions above the pigment in the coating.

5. The method of claim 1, which includes heating the pigment using an energy source selected from the group consisting of: a radiant heat, induction energy, hot air, open flame, at least one electric filament, at least one magnet, an infrared heat, and at least one laser.

6. The method of claim 1, which includes heating the pigment using conduction from the medical device and which includes heating the medical device using induction.

7. The method of claim 1, wherein the pigment is selected from a group consisting of: a phthalocyanine blue, a phthalocyanine green, a diarylide yellow, a diarylide orange, a quanacridone, a naphthol, a toluidine red, a carbizole violet, a carbon black, an iron oxide red, an iron oxide yellow, a chrome oxide green, a titanium oxide white, a cadmium red, a ultramarine blue, a moly orange, a lead chromate yellow, a mixed metal oxide, a talc, a calcium carbonate, a silicate and sulfate, a silica, a mica, an aluminum hydrate and silicate, a barium sulfate, a pearl pigment, a kaolin, an aluminum silicate derivative, an antomony trioxide, a metallic pigment, an aluminum flake pigment, and an iron oxide.

8. The method of claim 1, wherein the pigment is selected from a group consisting of a heat activated pigment, an organic pigment, an inorganic pigment, an extender pigment, a magnetic receptive pigment, and a laser excitable pigment.

9. The method of claim 1, wherein the coating includes a plurality of interspersed anti-microbial particles.

10. The method of claim 9, wherein the anti-microbial particles are selected from the group consisting of: silver particles, glass-silver particles, silver-ceramic particles, and ceramic particles.

11. The method of claim 1, wherein the medical device is selected from the group consisting of: a medical wire, a medical guide wire, a catheter, a needle, a biopsy device, a cannula, an electrosurgical electrode, a soft tissue needle, a soft tissue tubular device, a probe, and a blade.

12. The method of claim 1, wherein the binder is selected from the group consisting of: an epoxy, a phenoxy, a phenolic, a polyimide, apolyamide, a polyamide-amide, a polyarylsulfone, polyetheretherketone, polyetherketone, and a polyphenylene sulfide.

13. The method of claim 1, wherein the low-friction material is selected from the group consisting of: a polytetrafluoroethylene, a fluorinated ethylene propylene, a perfluoroalkoxy, a polyethylene, a silicone, a modified fluoropolymer, an irradiated polymer powder, and an irradiated polymer.

14. The method of claim 1, which includes applying an additional top coat to at least another portion of the low-friction top coat, said additional top coat including a plurality of particles of the low-friction material.

15. The method of claim 1, wherein applying the plurality of radiopaque particles to the at least one portion of the low-friction top coat includes applying the radiopaque particles to form at least one marking selected from the group consisting of: at least one line parallel to a longitudinal direction of the medical device, at least one line perpendicular to the longitudinal direction of the medical device, at least one line transverse to the longitudinal direction of the medical device and at least one line substantially transverse to the longitudinal direction of the medical device.

* * * * *